US012274732B2

(12) United States Patent
Guan et al.

(10) Patent No.: US 12,274,732 B2
(45) Date of Patent: Apr. 15, 2025

(54) ANTI-PATHOGEN COMPOSITION AND METHODS OF USE THEREOF

(71) Applicants: Tenfold Technologies, LLC, Pilot Point, TX (US); University of Mississippi, University, MS (US)

(72) Inventors: Shaohua Guan, Frisco, TX (US); Shashi Shankar Rajbanshi, Frisco, TX (US); Curtis Brian Hill, Little Elm, TX (US); Shi Qiu, Oxford, MS (US); Xing-Cong Li, Oxford, MS (US)

(73) Assignees: TENFOLD TECHNOLOGIES, LLC, Pilot Point, TX (US); UNIVERSITY OF MISSISSIPPI, University, MS (US)

( * ) Notice: Subject to any disclaimer, the term of this patent is extended or adjusted under 35 U.S.C. 154(b) by 443 days.

(21) Appl. No.: 16/498,901

(22) PCT Filed: Mar. 27, 2018

(86) PCT No.: PCT/US2018/024642
§ 371 (c)(1),
(2) Date: Sep. 27, 2019

(87) PCT Pub. No.: WO2018/183383
PCT Pub. Date: Oct. 4, 2018

(65) Prior Publication Data
US 2021/0085752 A1    Mar. 25, 2021

Related U.S. Application Data

(60) Provisional application No. 62/597,796, filed on Dec. 12, 2017, provisional application No. 62/570,919, filed on Oct. 11, 2017, provisional application No. 62/477,297, filed on Mar. 27, 2017.

(51) Int. Cl.
*A61K 38/16* (2006.01)
*C12N 1/20* (2006.01)

(52) U.S. Cl.
CPC .............. *A61K 38/164* (2013.01); *C12N 1/20* (2013.01)

(58) Field of Classification Search
None
See application file for complete search history.

(56) References Cited

U.S. PATENT DOCUMENTS

| | | |
|---|---|---|
| 5,075,109 A | 12/1991 | Tice et al. |
| 5,155,041 A | 10/1992 | Bok et al. |
| 6,015,553 A | 1/2000 | Germida et al. |
| 6,602,500 B1 | 8/2003 | Kharbanda et al. |
| 6,878,179 B2 | 4/2005 | Porubcan |
| 7,935,335 B2 | 5/2011 | Kochi et al. |
| 2003/0045428 A1 | 3/2003 | Porubcan |
| 2007/0248583 A1 | 10/2007 | Kochi et al. |
| 2014/0179521 A1 | 6/2014 | Fuller |
| 2016/0278388 A1 | 9/2016 | Beau et al. |
| 2017/0081631 A1 | 3/2017 | Maguire et al. |
| 2021/0106011 A1 | 4/2021 | Guan et al. |

FOREIGN PATENT DOCUMENTS

| | | |
|---|---|---|
| BR | PI06046029 A | 5/2008 |
| CN | 1095892 A | 12/1994 |
| CN | 1899047 A | 1/2007 |
| CN | 102786934 A | 11/2012 |
| CN | 105646015 A | 6/2016 |
| EP | 0705807 A1 | 4/1996 |
| JP | 62-273998 A | 11/1987 |
| JP | 62-273999 A | 11/1987 |
| JP | 2006-304684 A | 11/2006 |
| JP | 2011-519824 A | 7/2011 |
| JP | 2015-181423 A | 10/2015 |
| WO | WO-9639840 A2 | 12/1996 |
| WO | 2004/049778 A1 | 6/2004 |
| WO | 2012/161160 A1 | 11/2012 |
| WO | WO-2013050867 A2 | 4/2013 |
| WO | 2014/085576 A1 | 6/2014 |
| WO | 2015/156274 A1 | 10/2015 |
| WO | 2015/169919 A1 | 11/2015 |
| WO | WO-2016020371 A1 | 2/2016 |

OTHER PUBLICATIONS

New York State Department of Health (https://www.health.ny.gov/diseases/communicable/staphylococcus_aureus/methicillin_resistant/available online Nov. 2, 2007).*
The state of Rhode Island Department of Health (https://health.ri.gov/diseases/infectious/accessed Mar. 11, 22).*
Kajimura et al. ("Fusaricidin A, a new depsipeptide antibiotic produced by Bacillus polymyxa KT-8 Taxonomy, Fermentation, Isolation, Structure elucidation and biological activity" The Journal of Antibiotics vol. 49, No., 2, 1995).*
Vater et al. (Journal of Mass Spectrometry,, 52, 7-15, available online Nov. 22, 2016).*
Beatty et al., "Paenibacillus polymyxa produces fusaricidin-type antifungal antibiotics active against Leptosphaeria maculans, the causative agent of blackleg disease of canola", Canadian Journal of Microbiology, vol. 48, Mar. 3, 2002, pp. 159-169.

(Continued)

*Primary Examiner* — Julie Ha
*Assistant Examiner* — Tara L Martinez
(74) *Attorney, Agent, or Firm* — WILSON SONSINI GOODRICH & ROSATI

(57) ABSTRACT

Methods are provided for treating an infectious disease of a subject with a composition which comprises an active ingredient that can be produced by bacteria of *Paenibacillus* or *Bacillus*. The disclosure also provides a composition or a pharmaceutical composition which comprises, or alternatively consists essentially of, or yet further consists of an active ingredient which can be produced by bacteria of *Paenibacillus* or *Bacillus*.

11 Claims, 9 Drawing Sheets

(56) References Cited

OTHER PUBLICATIONS

Broders, K. (2007). Characterization of *Pythium* spp. Associated with Corn and Soybean Seed and Seedling Disease in Ohio. Plant Disease, 91(6):727-735.
Brown, G. D., et al. (2012). Tackling Human Fungal Infections. Science Translational Medicine, Editorial, 4(165):647.
De Farias Neto, A. L., et al. (Nov.-Dec. 2006). Irrigation and Inoculation Treatments that Increase the Severity of Soybean Sudden Death Syndrome in the Field. Crop Science, 46:2547-2554.
Fu et al., "Identification of a plant growth promoting bacterium", NCBI, Sep. 2015 (PDF not available).
George-Okafor et al., "Screening and Optimal Protease Production by *Bacillus* sp. Sw-2 Using Low Cost Substrate Medium," Research Journal of Microbiology, 7(7): 327-336 (2012).
Goris, J., et al. (2007). DNA-DNA hybridization values and their relationship to whole-genome sequence similarities. International Journal of Systematic and Evolutionary Microbiology, 57:81-91.
Hamilton-Miller, J. M. T. (Jun. 1973). Chemistry and Biology of the Polyene Macrolide Antibiotics. American Society for Microbiology, Bacteriological Reviews, 37(2):166-196.
Haron et al., "Quantitative determination and pharmacokinetic study of fusaricidin A in mice plasma and tissues using ultra-high performance liquid chromatography-tandem mass spectrometry", Journal of Pharmaceutical and Biomedical Analysis, vol. 170, 2019, pp. 187-192.
International Preliminary Report on Patentability received for PCT Patent Application No. PCT/US2018/024638, mailed on Oct. 10, 2019, 8 pages.
International Preliminary Report on Patentability received for PCT Patent Application No. PCT/US2018/024642, mailed on Oct. 10, 2019, 11 pages.
International Search Report and Written Opinion received for PCT Patent Application No. PCT/US2018/024638, mailed on Jul. 20, 2018, 10 pages.
International Search Report and Written Opinion received for PCT Patent Application No. PCT/US2018/024642, mailed on May 15, 2018, 12 pages.
Kajimura et al., "Fusaricidin A, a new depsipeptide antibiotic produced by Bacillus polymyxa KT-8.Taxonomy, fermentation, isolation, structure elucidation and biological activity", The Journal of Antibiotics, vol. 49, No. 2, Feb. 1, 1996, pp. 129-135.
Klevens, R. M., et al. (March-Apr. 2007). Estimating Health Care-Associated Infections and Deaths in U.S. Hospitals, 2002. Public Health Records, 122:160-166.
Lee et al., "An antibiotic fusaricidin: a cyclic depsipeptide from Paenibacillus polymyxa E681 induces systemic resistance against Phytophthora blight of red-pepper," Phytoparasitica, 41:49-58 (2013).
Lee et al., "Mannheimia succiniciproducens Phosphotransferase System for Sucrose Utilization", Applied and Environmental Microbiology, vol. 76, No. 5, Mar. 2010, pp. 1699-1703.
Mamun et al., "Optimization of fermenting medium by statistical method for production of alkaline protease by Bacillus licheniformis MZK05M9", Journal of Applied Biology & Biotechnology, 5(6):24-28 (Nov.-Dec. 2017).
Mukhtar et al., "Comparative Evaluation of Agroindustrial Byproducts for the Production of Alkaline Protease by Wild and Mutant Strains of Bacillus subtilis in Submerged and Solid State Fermentation," Hindawi Publishing Corporation the Scientific World Journal, vol. 2013, Article ID 538067, 6 pages.
Qiu et al., "Identification of fusaricidins from the antifungal microbial strain *Paenibacillus sp.* MS2379 using ultra-high performance liquid chromatography coupled to quadrupole time-of-flight mass spectrometry", Journal of Chromatography A, vol. 1586, Dec. 5, 2018, pp. 91-100.
Silva et al., "Production of Bio-inseticide *Bacillus thuringiensis var.* israelensis in Semicontinuous Processes Combined with Batch Processes for Sporulation," Braz. Arch. Biol. Technol., 54(1):45-52, (Jan./Feb. 2011).
Smith, K. D. (Dec. 2015). Increased Antifungal Drug Resistance in Clinical Isolates of Cryptococcus neoformans in Uganda. Antimicrobial Agents and Chemotherapy, 59(12):7197-7204.
Song, J. L., et al. (Apr. 2004). The Candida albicans Lanosterol 14-alpha-Demethylase (ERG11) Gene Promoter Is Maximally Induced after Prolonged Growth with Antifungal Drugs. Antimicrobial Agents and Chemotherapy, 48:1136-1144.
Vater et al., "Characterization of Novel Fusaricidins Produced by Paenibacillus polymyxa-M1 Using MALDI-TOF Mass Spectrometry", Journal of American Society of Mass Spectrometry, vol. 26, Jun. 23, 2015, pp. 1548-1558.
Extended European Search Report and Written Opinion received for EP Patent Application No. 18775154, mailed on May 3, 2021, 11 pages.
Extended European Search Report and Written Opinion received for EP Patent Application No. 18777897, mailed on Dec. 16, 2020, 10 pages.
Notice of Reasons for Refusal received for Japanese Application No. 2019-553033, mailed on Nov. 9, 2021, 4 pages (2 pages of English Translation and 2 pages of Original Document).
U.S. Patent and Trademark Office; Non-Final Office Action; U.S. Appl. No. 16/498,937; dated Jun. 2, 2022.
De Souza, Rocheli et al.; Plant growth-promoting bacteria as inoculants in agricultural soils; 2015.
Brazilian Patent Office; Official Action with machine English translation; BR Application No. BR112019020151-3; issued May 17, 2022.
Kuroda, Jun et al.; Li-F Antibiotics, a Family of Antifungal Cyclic Depsipeptides Produced By Bacillus Polymyxa L-1129; 2000.
Cochrane, Stephen A. et al.; Lipopeptides from *Bacillus* and *Paenibacillus* spp.: A Gold Mine of Antibiotic Candidates; 2016.
Yu, Wen-Bang et al.; Prediction of the Mechanism of Action of Fusaricidin on Bacillus subtilis; 2012.
Yang, Anming et al.; Characterization and antifungal activity against Pestalotiopsis of a fusaricidin-type compound produced by Paenibacillus polymyxa Y-1; 2018.
De Souza, et al. Plant growth-promoting bacteria as inoculants in agricultural soils. Genetics and Molecular Biology 38(4):401-419 (2015).
Fukuda, et al. Production improvement of antifungal, antitrypanosomal nucleoside sinefungin by rpoB mutation and optimization of resting cell system of Streptomyces incarnatus NRRL 8089. J Biosci Bioeng 109(5):459-465 (2010).
Kilani-Feki, et al. Improvement of antifungal metabolites production by Bacillus subtilis V26 for biocontrol of tomato postharvest disease. Biological Control 95: 73-82 (2016).
Liu, et al. Optimization for the production of surfactin with a new synergistic antifungal activity. PLoS One 7(5):e34430, 1-9 (2012).
Mendizabal, et al. Production of the postharvest biocontrol agent Bacillus subtilis CPA-8 using low cost commercial products and by-products. Biological Control 60(3): 280-289 (2012).
Mezghanni, et al. Medium optimization of antifungal activity production by Bacillus amyloliquefaciens using statistical experimental design. Prep Biochem Biotechnol 42(3):267-278 (2012).

\* cited by examiner

| Sample Name | Code | C. albicans IC50 | C. glabrata IC50 | C. krusei IC50 | A. fumigatus IC50 | C. neoformans IC50 | S. aureus IC50 | MRS IC50 | E. coli IC50 | P. aeruginosa IC50 | M. intracellulare IC50 |
|---|---|---|---|---|---|---|---|---|---|---|---|
| Amphotericin B | AMB | 0.06 | 0.09 | 0.12 | 0.33 | 0.15 | | | | | |
| Ciprofloxacin | CIPRO | | | | | | 0.11 | 0.1 | 0.01 | 0.07 | 0.39 |
| MS2414 column fraction 7 | RRR-6-78B | >20 | >20 | >20 | >20 | >20 | >20 | >20 | >20 | >20 | >20 |
| MS2414 column fraction 8-9 | RRR-6-78C | >20 | >20 | >20 | >20 | >20 | >20 | >20 | >20 | >20 | >20 |
| MS2414 column fraction 10-12 | RRR-6-78D | >20 | >20 | >20 | >20 | >20 | >20 | >20 | >20 | >20 | >20 |
| MS2414 column fraction 13-15 | RRR-6-78E | >20 | >20 | >20 | >20 | 0.9 | >20 | >20 | >20 | >20 | >20 |
| MS2414 column fraction 16-20 | RRR-6-78F | >20 | >20 | >20 | >20 | >20 | >20 | >20 | >20 | >20 | >20 |
| MS2414 column fraction 21-24 | RRR-6-78G | >20 | >20 | >20 | >20 | >20 | >20 | >20 | >20 | >20 | >20 |
| MS2414 column fraction 25-28 | RRR-6-78H | >20 | >20 | >20 | >20 | >20 | >20 | >20 | >20 | >20 | >20 |
| MS2414 column fraction 29-34 | RRR-6-78I | >20 | >20 | >20 | >20 | >20 | >20 | >20 | >20 | >20 | >20 |
| MS2414 column fraction 35-40 | RRR-6-78J | >200 | >200 | >200 | >200 | >200 | >200 | >200 | >200 | >200 | |
| MS2414 column fraction 41-46 | RRR-6-78K | >20 | >20 | >20 | >20 | >20 | >20 | >20 | >20 | >20 | >20 |
| MS2414 column fraction 47-50 | RRR-6-78L | >20 | >20 | >20 | 11.38 | >20 | >20 | >20 | >20 | >20 | |
| MS2414 column fraction 51-56 | RRR-6-78M | >20 | >20 | >20 | >20 | >20 | >20 | >20 | >20 | >20 | >20 |
| MS2414 column fraction 57-62 | RRR-6-78N | >20 | >20 | >20 | >20 | >20 | >20 | >20 | >20 | >20 | >20 |
| MS2414 column fraction 63-66 | RRR-6-78O | >20 | >20 | >20 | >20 | >20 | >20 | >20 | >20 | >20 | >20 |
| MS2414 column fraction 67-72 | RRR-6-78P | >20 | >20 | >20 | >20 | >20 | >20 | >20 | >20 | >20 | >20 |
| MS2414 column fraction 73-85 | RRR-6-78Q | >20 | >20 | >20 | >20 | >20 | >20 | >20 | >20 | >20 | >20 |
| MS2414 column fraction 86-93 | RRR-6-79A | >20 | >20 | >20 | >20 | >20 | >20 | >20 | >20 | >20 | >20 |
| MS2414 column fraction 94-96 | RRR-6-79B | >20 | >20 | >20 | >20 | 14.8 | >20 | >20 | >20 | >20 | >20 |
| MS2414 column fraction 107-114 | RRR-6-79D | >20 | >20 | >20 | >20 | >20 | >20 | 4.43 | >20 | >20 | >20 |
| MS2414 column fraction 115-118 | RRR-6-79E | >20 | >20 | >20 | >20 | 2.49 | 10.53 | 10.11 | >20 | >20 | >20 |
| MS2414 column fraction 119-123 | RRR-6-79F | >20 | >20 | >20 | >20 | 0.32 | 11.01 | 4.17 | >20 | >20 | 2.45 |
| MS2414 column fraction 124-130 | RRR-6-79G | 78.18 | >200 | 29.82 | >200 | <0.06 | 1.82 | 0.35 | >200 | >200 | 0.46 |
| MS2414 column fraction 131-135 | RRR-6-79H | 8.79 | 25.29 | 3.65 | >200 | <0.06 | 0.34 | 1.66 | >200 | >200 | 0.69 |
| MS2414 column fraction 136-152 | RRR-6-79I | 6.6 | 200 | 3.98 | >200 | 0.46 | 1.23 | 5.95 | >200 | >200 | 5.28 |
| MS2414 column fraction 153-162 | RRR-6-79J | 11.13 | 58.56 | 10.46 | >200 | 2.12 | 7.97 | 1.16 | >200 | >200 | 0.45 |
| MS2414 column fraction 163-168 | RRR-6-79K | >200 | >200 | >200 | >200 | 8.66 | 5.68 | 10.66 | >200 | >200 | 42.42 |
| MS2414 column fraction 170-173 | RRR-6-79M | >200 | >200 | >200 | >200 | 35.64 | 27.95 | 52.32 | >200 | >200 | 127.85 |
| MS2414 column fraction 174-178 | RRR-6-79N | >200 | >200 | >200 | >200 | 0.42 | 38 | 1.95 | >200 | >200 | 22.1 |
| MS2414 column fraction 179-181 | RRR-6-79O | >200 | >200 | >200 | >200 | 19.28 | 2.34 | 31.67 | >200 | >200 | <8 |
| n-BuOH extract of MS2414 in GB6-M | RRR-6-77A | | 49.84 | 52.45 | >200 | <8 | 86.33 | <8 | 19.78 | >200 | <8 |
| MeOH extract of MS2414 in GB6-M | RRR-6-77I | >200 | >200 | 41.99 | >200 | <8 | <8 | <8 | >200 | >200 | <8 |
| MeOH extract of MS2414 in GB6-M P | RRR-6-77I | >200 | >200 | >200 | >200 | 19.73 | 37.67 | 27.24 | 10.08 | 28.37 | 35.25 |
| n-BuOH extract of MS2414 in BS3-M2 | RRR-6-77B | >200 | >200 | >200 | >200 | 17.89 | 17.8 | 27.85 | 47.89 | 193.03 | 65.91 |
| n-BuOH extract of MS2414 in BS3-M2 | RRR-6-77B | >200 | >200 | >200 | >200 | <8 | <8 | <8 | >200 | >200 | <8 |
| MeOH extract of MS2414 in BS3-M2 | RRR-6-77J | >200 | 53.96 | 49.95 | >200 | 9.68 | <8 | <8 | >200 | >200 | <8 |
| MeOH extract of MS2414 in BS3-M2 | RRR-6-77J | >200 | >200 | 11 | >200 | | | | | | |

*MS2414 column fractions are derived from the MeOH extract of MS2414 in BS3-M2*

FIG. 6

| Fraction | C. albicans | C. glabrata | C. krusei | C. neoformans | S. aureus | MRS | M. intracellulare | Test Conc |
|---|---|---|---|---|---|---|---|---|
| RRR-6-79G | 78.18 | >200 | 29.82 | 0.32 | 1.82 | 4.17 | 2.45 | 200-0.06 |
| RRR-6-79H (83U) | 8.79 | 25.29 | 3.65 | <0.06 | 0.34 | 0.35 | 0.46 | 200-0.06 |
| RRR-6-79I (83V) | 8.6 | 200 | 3.98 | <0.06 | 1.23 | 1.66 | 0.06 | 200-0.06 |
| RRR-6-79J | 11.13 | 58.56 | 10.46 | 0.46 | 7.97 | 5.95 | 5.28 | 200-0.06 |
| RRR-6-79K | >200 | >200 | >200 | 2.12 | 5.58 | 1.16 | 0.45 | 200-0.06 |
| RRR-6-79M | >200 | >200 | >200 | 8.66 | 27.95 | 10.66 | 42.42 | 200-0.06 |
| RRR-6-79N | >200 | >200 | >200 | 35.64 | 36 | 52.32 | 127.85 | 200-0.06 |
| RRR-6-79O | >200 | >200 | >200 | 0.42 | 2.34 | 1.95 | 22.1 | 200-0.06 |
FIG. 7
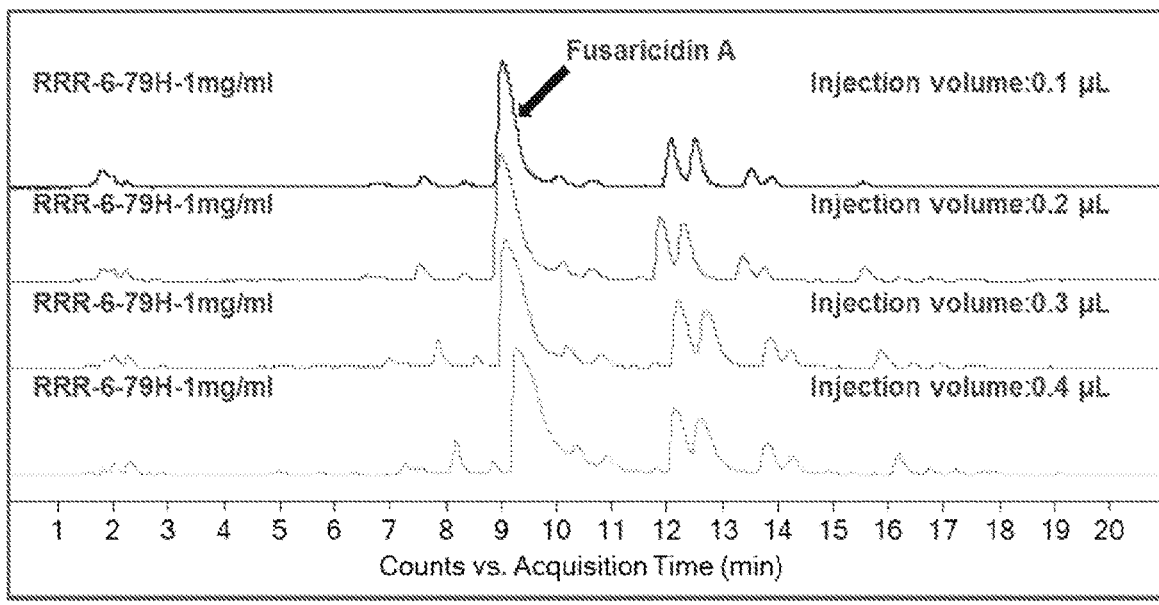
FIG. 8A
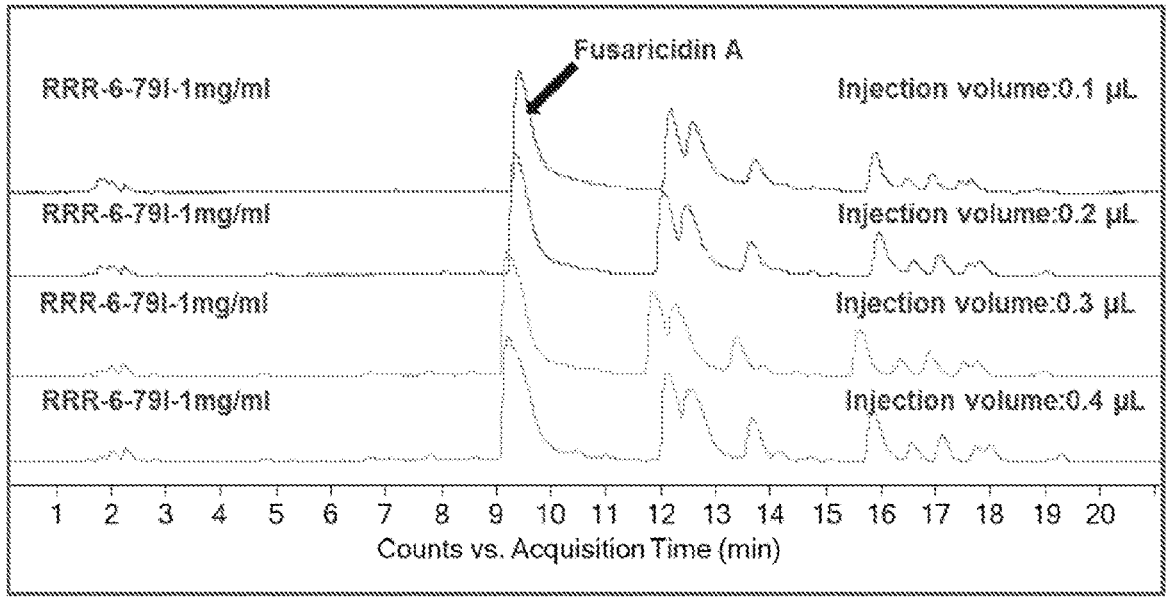
FIG. 8B

ANTI-PATHOGEN COMPOSITION AND METHODS OF USE THEREOF

CROSS-REFERENCE TO RELATED PATENT APPLICATIONS

This application is a national phase application under 35 U.S.C. § 371 of PCT Application No. PCT/US2018/024642, filed on Mar. 27, 2018, which claims priority under 35 U.S.C. § 119(e) to U.S. Provisional Application Nos. 62/477,297, filed Mar. 27, 2017, 62/570,919, filed on Oct. 11, 2017, and 62/597,796, filed on Dec. 12, 2017. The content of each of these applications is hereby incorporated by reference in its entirety.

BACKGROUND

Infectious diseases remain the predominant cause of death in humans and animals in both developed and, more alarmingly, developing countries in Africa, Asia, the Caribbean, and South America. Currently, three infectious diseases (lower respiratory infections, HIV/AIDS, and diarrheal diseases) are ranked in the top ten causes of death by the World Health Organization. For example, lower respiratory infections alone account for 3.1 million deaths each year globally. In the U.S., even with its state-of-the-art health care system, lower respiratory infections remain the third leading cause of death, behind only heart disease and cancer. In addition, the communicative nature of the diseases poses enormous challenges for controlling or eradicating infectious diseases in public. For example, diarrhea, caused partly by contaminated food and drinks, affects 40-50% of visitors from industrialized countries travelling to developing countries which, due to lack of financial resources, already face enormous pressure to implement large-scale preventive measures to control the transmission of the disease.

Infectious diseases are primarily caused by microorganisms or pathogens, such as viruses, bacteria, fungi, and parasites. Once transmitted to a host (e.g., a human or animal), pathogens may disrupt the normal physiological process of the host and stimulate immune responses, e.g., inflammation, fever, or other symptoms. Invasive infectious mycoses are among the most significant and common invasive fungal infections, which emerge worldwide and mainly include Aspergillosis (*Aspergillus fumigatus*), Candidiasis (*Candida albicans*), Cryptococcosis (*Cryptococcus neoformans*), Mucormycosis (*Rhizopus oryzae*), and Pneumocystis (*Pneumocystis jirovecii*). Brown et al., *Sci Transl Med.*, 4(165) (2012). Among them, Aspergillosis clearly remains the most common mold infection in patients with hematological cancer, with *Aspergillus fumigatus* being the offending cause in more than 90% of the infected patients. Cryptococcosis, which is most commonly caused by *C. neoformans*, causes more than 1 million cases of infections worldwide with a mortality rate as high as 70% for the infected population. Cryptococcal meningitis, one of the most common Cryptococcal diseases, leads to 15% to 20% of AIDS-related mortality, largely due to inaccurate diagnosis, ineffective treatment, and the emerging resistance to antifungal agents. Smith et al., *Antimicrob. Agents Chemother.*, vol. 59 no. 12 7197-7204 (2015).

Over the decades, a number of agents or treatments have been developed to combat infectious diseases. However, the emergence of antimicrobial resistance in the pathogens poses a major threat to public health. For example, a majority of infections contracted in hospitals (the so-called nosocomial infections) are caused by a small number of resistant bacteria species, which are collectively called "ESKAPE" pathogens (*Enterococcus faecium, Staphylococcus aureus, Klebsiella pneumoniae, Acinetobacter baumannii, Pseudomonas aeruginosa*, and *Enterobacter* sp.). See Rice L., *The Journal of Infectious Diseases*, 197(8), 1079-1081 (2008). Most of the ESKAPEs are multiple-drug resistant isolates. Despite the great risk posed to elderly, vulnerable patients by ESKAPE, the current treatments for the pathogens are extremely limited such that doctors often have to resort to outdated or even discarded therapeutics (e.g., colistin) for treatment. But the toxicity of the old therapeutics may subject those patients to additional suffering and pain. Moreover, the lack of guidance on an effective dosage regimen for the old therapeutics undermines their effects on ESKAPEs. It was estimated that ESKAPE infection has contributed to the death of about 99,000 patients per year, with about 1.7 million patients suffering from it. Klevens et al., *Public Health Reports*, vol. 122, no. 2, pp. 160-166 (2007).

Four major classes of antifungal agents are commonly used to combat the fungal infections—polyenes, azoles, pyrimidines, and echinocandins. The modes of action for all the antifungals are to inhibit the fungal growth or induce fungal cell death. For example, polyenes (e.g., Amphotericin B, nystatin, and natamycin) can interact with ergosterol on fungal membrane and disrupt the cytoplasmic membrane. The release of K+ and Na+ ions through the disrupted membrane leads to the death of fungal cells. Hamilton-Miller, Bacteriological Reviews, 37 (2): 166-196 (1973). Pyrimidine and its analogs (e.g., flucytosine) can disrupt DNA and protein synthesis by incorporating itself into RNA, which results in cell death. Barker et al., *Curr Infect Dis Rep.*, 8:449-56 (2006). Echinocandin antifungals can inhibit the synthesis of glucan, an integral component of the cell walls of fungi. Morris et al., *Am J Health Syst Pharm.*, 63 (18): 1693-703 (2006). Azoles, including fluconazole and voriconazole, can target lanosterol 14-alpha-demethylase and inhibit the biosynthesis of ergosterol, leading to the dysfunction or disruption of fungal membranes. Song et al., *Antimicrob Agents Chemother., April*, 48(4):1136-44 (2004).

However, the suboptimal results from the currently available antifungals highlight the need for alternative antifungals for safer and more effective treatment. Treatments with either polyenes or pyrimidine analogs are often complicated by their high toxicity. For example, pyrimidine analogs can induce hematologic toxicity in patients. Even with relatively low toxicity, patients treated with azoles may rapidly develop resistance to treatment. As for echinocandin products, they show comparable antifungal activities as azole products, but the poor solubility of the antifungals limits their delivery options and absorption rates. The World Health Organization (WHO) guidelines recommend the use of fluconazole for preemptive treatment of asymptomatic cryptococcal antigen-positive persons with CD4 counts of <100 cells/µl who have early subclinical cryptococcosis infection. However, the increased incidences of fluconazole resistance in third-world countries over the past decade may impact the clinical utility of this drug. Smith et al., *Antimicrob. Agents Chemother.*, vol. 59 no. 127197-7204 (2015).

Therefore, there exists a need for an effective, new therapeutic composition against a broad spectrum of microorganisms, specifically those drug-resistant pathogens.

SUMMARY OF THE INVENTION

In one aspect, the disclosure relates to compositions for treating an infectious disease or a pathogen comprising, consisting essentially of, or consisting of a fusaricidin. In one embodiment, the fusaricidin is a cyclic fusaricidin or an open-chain fusaricidin. In some embodiments, the cyclic fusaricidin is a compound of Formula I:

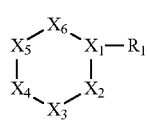

Formula I wherein $X_1$ is Thr or Ser; $X_2$ is Val or Ile; $X_3$ is selected from a group consisting of Val, Ile, Tyr, and Phe; $X_4$ is Thr or Ser; $X_5$ is Asn or Gln; $X_6$ is Ala; wherein $R_1$ is a GHPD side chain or GHID side chain.

In some embodiments, the open-chain fusaricidin is a compound of Formula II:

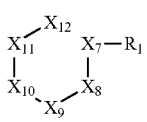

Formula II wherein $X_7$ is Thr or Ser; $X_8$ is Val or Ile; $X_9$ is selected from a group consisting of Val, Ile, Tyr, and Phe; $X_{10}$ is Thr or Ser; $X_{11}$ is Asn or Gln; $X_{12}$ is selected from a group consisting of Ala, GABA, and Gly; wherein $R_1$ is a GHPD side chain. The fusaricidin, in some embodiments, is the same or similar to a metabolite produced by bacteria of *Paenibacillus* or *Bacillus*. The bacteria comprise, consist essentially of, or yet consist of MS1479, MS2379, MS2414, MS2820, MS0633, MS2335, MS2652, MS2658, MS2681, MS2697, or MS2712. A sample of each bacterial strain has been deposited with the American Type Culture Collection (ATCC®), Manassas, VA, USA. The bacterial isolates or their mutants of this disclosure may be genetically modified or not genetically modified.

The disclosure is directed to methods for treating an infectious disease of a subject comprising administering to the subject an effective amount of a fusaricidin or a bacterium. In one embodiment, the fusaricidin comprises a cyclic fusaricidin or an open-chain fusaricidin. The fusaricidin, in some embodiments, is the same or similar to a metabolite produced by bacteria of *Paenibacillus* or *Bacillus*. The bacteria comprise, consist essentially of, or yet consist of MS1479, MS2379, MS2414, MS2820, MS0633, MS2335, MS2652, MS2658, MS2681, MS2697, or MS2712. A sample of each bacterial strain has been deposited with the American Type Culture Collection (ATCC®), Manassas, VA, USA.

In another aspect, the disclosure also relates to a method of producing fursaricidin and a method of treating an infectious disease or a pathogen.

BRIEF DESCRIPTION OF THE DRAWINGS

FIG. 2A shows the in vitro inhibition of *E. cloacae*. FIG. 2B shows the in vitro inhibition of *P. aeruginosa*.

FIG. 6 shows the antimicrobial activities of extracts and column fractions of microbial strain MS2414 and the commercially available antimicrobial agents (amphotericin B and ciprofloxacin).

FIG. 7 shows the antimicrobial activities of column fractions of MS2414 (IC50, g/ml).

FIGS. 8A and 8B show LC-MS chromatograms of RP-18 column fractions of RRR-6-79H and RRR-6-79I of MS2414.

DETAILED DESCRIPTION

Figure 1:
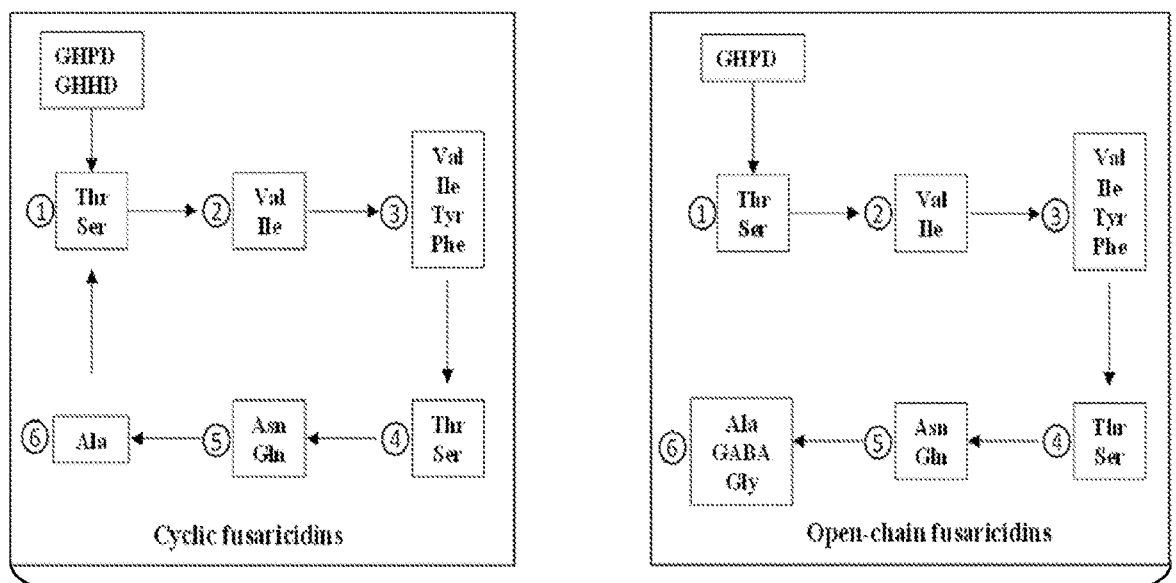
FIG. 1 depicts the diagrammatic structures of fusaricidins.

After reading this description, it will become apparent to one skilled in the art how to implement the disclosure in various alternative embodiments and alternative applications. However, not all embodiments of the present disclosure are described herein. It will be understood that the embodiments presented here are presented by way of example only, and not limitation. As such, this detailed description of various alternative embodiments should not be construed to limit the scope or breadth of the present disclosure as set forth below.

Before the present disclosure is disclosed and described, it is to be understood that the aspects described below are not limited to specific compositions, methods of preparing such compositions, or uses thereof, and as such may, of course, vary. It is also to be understood that the terminology used herein is for the purpose of describing particular aspects only, and is not intended to be limiting.

Throughout this disclosure, various publications, patents, and published patent specifications are referenced by an identifying citation. The disclosures of these publications, patents, and published patent specifications are hereby incorporated by reference in their entirety into the present disclosure.

Definitions

Unless defined otherwise, all technical and scientific terms used herein have the same meaning as commonly understood by one of ordinary skill in the art to which this disclosure belongs.

In this specification and in the claims that follow, reference will be made to a number of terms that shall be defined to have the following meanings:

The terminology used herein is for the purpose of describing particular embodiments only, and is not intended to be limiting of the disclosure. As used herein, the singular forms "a," "an," and "the" are intended to include the plural forms as well, unless the context clearly indicates otherwise.

All numerical designations, e.g., pH, temperature, time, concentration, amounts, and molecular weight, including ranges, are approximations which are varied (+) or (−) by 10%, 1%, or 0.1%, as appropriate. It is to be understood, although not always explicitly stated, that all numerical designations may be preceded by the term "about." It is also to be understood, although not always explicitly stated, that the reagents described herein are merely exemplary and that equivalents of such are known in the art.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about," when used with regard to a dose amount, means that the dose may vary by +/−10%.

The term "comprising" or "comprises" is intended to mean that the compositions and methods include the recited elements but do not exclude others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claimed disclosure. "Consisting of" shall mean excluding more than trace amounts of other ingredients and substantial method steps recited. Embodiments defined by each of these transition terms are within the scope of this disclosure.

The term "ESKAPE" refers to *Enterococcus faecium, Staphylococcus aureus, Klebsiella pneumoniae, Acinetobacter baumannii, Pseudomonas aeruginosa,* and *Enterobacter* sp. ESKAPE pathogens are implicated in nosocomial infection. In some embodiments, ESKAPE pathogens are antibiotic resistant. "Nosocomial infection" or "hospital-acquired infection" (HAI) refers to an infection developed in a hospital or healthcare environment. In some embodiments, a nosocomial infection is a fungal, bacterial, viral, or parasitic infection. In one embodiment, nosocomial infection can cause severe pneumonia as well as infections of the urinary tract, bloodstream, and other parts of the body. Nosocomial infections can pose serious health concerns for patients and care providers.

As used herein, the term "active ingredient" refers to a biologically active substance, and examples thereof include a compound, a protein, a peptide, a cyclic peptide, a nucleic acid, a nanoparticle, anticancer drugs, anti-pathogen drugs, anti-infection drugs, anti-angiogenesis inhibitors, anti-inflammatory drugs, analgesics, antiarthritics, sedatives, antidepressants, antipsychotics, tranquilizers, antianxiety drugs, narcotic antagonists, anti-Parkinson's disease drugs, cholinergic agents, immunosuppressive agents, antiviral agents, antibiotics, appetite suppressants, anticholinergics, antihistamines, anti-migraine drugs, hormones, vasodilators, birth control pills, antithrombotic agents, diuretics, antihypertensives, cardiovascular drugs, wrinkle-diminishing agents, inhibitors of skin aging, skin whitening agents, or any combination thereof. In one embodiment, the active ingredient is produced by an organism or synthesized. In some embodiments, the active ingredient can be used to treat a pathogen or an infectious disease. In some embodiments, the active ingredient includes but is not limited to fusaricidins and/or their derivatives and analogs.

The term "treating" or "treatment" covers the treatment of a disease described herein in a subject, and includes: (i) inhibiting a disease, i.e., arresting its development; (ii) relieving a disease; (iii) slowing progression of the disease; (iv) inhibiting, relieving, or slowing progression of one or more symptoms of the disease or disorder; and/or (v) reducing the growth of the disease causing organism, e.g., pathogens.

The term "administering" or "administration" refers to any mode of application of a composition, an inhibitory agent, or a drug to a subject in need of treatment. While the compositions described herein may be suitable for administration via any route, exemplary administration routes include, but are not limited to, oral, rectal, ophthalmic (including intravitreal or intracameral), nasal, topical (including buccal and sublingual), intrauterine, vaginal, or parenteral (including subcutaneous, intraperitoneal, intramuscular, intravenous, intradermal, intracranial, intratracheal, and epidural) administration.

It is also to be appreciated that the various modes of treatment or prevention of medical diseases and conditions as described are intended to mean "substantial," which includes total, but also less than total, treatment or prevention, and wherein some biologically or medically relevant result is achieved.

As used herein, the term "effective amount" refers to an amount of composition which is capable of inhibiting, relieving, and/or suppressing diseases or symptoms. In some embodiments, the precise effective amount will vary based on the type of the subject, the diseases, the level of infections, and/or the types of pathogens or microbes that cause the infectious diseases. In some embodiments, the effective amount is an amount of formulation, composition, or reagent in a pharmaceutical acceptable carrier that is of sufficient quantity to ameliorate the state of the patient or animal so treated. The term "ameliorate" refers to a lessening of the detrimental effect of the disease state or disorder in the recipient of the therapy. The term "modulate" means enhance, inhibit, alter, or modify the expression or function of antimicrobial activity in combination with a pharmaceutically acceptable carrier. The subject of the disclosure can be a human or any animal and can be treated in the methods or composition of this disclosure.

As used herein, the terms "disease" and "condition" refer to an interruption, cessation, or deviation from the normal structure or function of any part, organ, or system of the body. One skilled in the art can readily recognize signs or symptoms associated with a disease or condition and can readily recognize the amelioration of an associated sign and/or symptom. The methods of the disclosure can be applied to the treatment of a variety of pathogen-induced diseases or conditions as described in further detail below.

Pathogenic infection refers to the colonization and/or invasion and multiplication of pathogenic microorganisms in the host with or without the manifestation of disease.

As used herein, the term "fungicide" means any agents, compositions, compounds, biologics, and chemicals that can inhibit, suppress, and/or limit the functions, growth, or pathogenic activities of a fungal species.

As used herein, the term "bactericide" means any agents, compositions, compounds, biologics, and chemicals that can inhibit, suppress, and/or limit the functions, growth, or pathogenic activities of a bacterial species.

As used herein, the term "microbe" or "microbial" refers to any organism that is microscopic or too small to be seen by the naked human eye.

As used herein, the term "pathogen" refers to any infectious microbes causing disease in an organism. In one embodiment, the pathogens comprise bacteria, fungi, archaea (e.g., methanogens, halophiles, thermophiles, and psychrophiles), protists (e.g., *Plasmodium, Entamoeba histolytica, Trypanosoma brucei, Giardia lamblia*), viruses, prions (e.g., PrP$^{res}$ and PrP$^{Sc}$), microscopic plants (e.g., *Shewanella algae, Shewanella putrefaciens,* and *Shewanella xiamenensis*), and/or microscopic animals (e.g., plankton and planarian). In some embodiments, the viruses include but are not limited to RNA viruses such as flaviviruses, picornaviruses, rhabdoviruses, filoviruses, retroviruses (including lentiviruses), or DNA viruses such as adenoviruses, poxviruses, herpes viruses, cytomegaloviruses, hepadnaviruses, or others. In some embodiments, pathogens include bacteria, fungi, helminths, schistosomes, and trypanosomes. Other kinds of pathogens can include mammalian transposable elements.

The bacteria include but are not limited to "ESKAPE" pathogens *Enterococcus faecium, Staphylococcus aureus, Klebsiella pneumoniae, Acinetobacter baumannii, Pseudomonas aeruginosa,* and *Enterobacter* sp. In some embodiments, bacteria include, but are not limited to, *Actinomyces israelii, Bacillus anthracis, Bacteroides fragilis, Bordetella pertussis, B. burgdorferi, B. garinii, B. afzelii, B. abortus, B. canis, B. melitensis, B. suis, Campylobacter jejuni, C. trachomatis, C. pneumoniae, Chlamydophila psittaci, C. botulinum, C. difficile, C. perfringens, C. tetani, Corynebacterium diphtheriae, E. canis, E. chaffeensis, E. faecalis, E. faecium, E. coli,* Enterotoxigenic *E. coli* (ETEC), Enteropathogenic *E. coli*, Enteroinvasive *E. coli* (EIEC), Enterohemorrhagic *E. coli* (EHEC), *Francisella tularensis, Haemophilus influenzae, Helicobacter pylori, Klebsiella pneumoniae, Legionella pneumophila, Leptospira species, Listeria monocytogenes, M. leprae, M. tuberculosis, Mycoplasma pneumoniae, N. gonorrhoeae, N. meningitidis, Pseudomonas aeruginosa, Nocardia asteroides, Rickettsia rickettsii, Salmonella typhi, S. typhimurium, S. sonnei, S. dysenteriae, Staphylococcus aureus, Staphylococcus epidermidis, Staphylococcus saprophyticus, Streptococcus agalactiae, Streptococcus pneumoniae, Streptococcus pyogenes, Streptococcus viridans, Treponema pallidum, Vibrio cholerae,* and *Yersinia pestis*.

Non-limiting examples of fungi include *Absidia corymbifera* or *ramosa, Achorion gallinae, Actinomadura* spp., *Actinomyces* spp., *Ajellomyces dermatitidis, Aleurisma brasiliensis, Alleschería boydii, Arthroderma* spp., *Aspergillus* spp., *Basidiobolus* spp., *Blastomyces* spp., *Cadophora* spp., *Candida albicans, Cercospora apii, Chrysosporium* spp., *Cladosporium* spp., *Cladothrix asteroids, Coccidioides immitis, Cryptococcus neoformans, Cunninghamella elegans, Dematium wernecke, Discomyces israelii, Emmonsia* spp., *Emmonsiella capsulate, Endomyces geotrichum, Entomophthora coronata, Epidermophyton floccosum, Filobasidiella neoformans, Fonsecaea* spp., *Geotrichum candidum, Glenospora khartoumensis, Gymnoascus gypseus, Haplosporangium parvum, Histoplasma* spp., *Hormiscium dermatitidis, Hormodendrum* spp., *Keratinomyces* spp., *Langeronia soudanense, Leptosphaeria senegalensis, Lichtheimia corymbifera, Lobmyces loboi, Loboa loboi, Lobomycosis, Madurella* spp., *Malassezia furfur, Micrococcus pelletieri, Microsporum* spp. (ringworm), *Monilia* spp., *Mucor* spp., *Mycobacterium tuberculosis, Nannizzia* spp., *Neotestudina rosati, Nocardia* spp., *Oidium albicans, Oospora lactis, Paracoccidioides brasiliensis, Petriellidium boydii, Phialophora* spp., *Piedraia hortae, Pityrosporum furfur, Pullularia gougerotii, Pyrenochaeta romeroi, Rhinosporidium seeberi, Sabouraudites (Microsporum), Sartorya fumigate, Sepedonium, Sporotrichum* spp., *Streptomyces* spp., *Tinea* spp. (ringworm), *Torula* spp., *Trichophyton* spp. (ringworm), *Trichosporon* spp., and *Zopfia rosatii*.

Non-limiting examples of viruses include Adenovirus; Coxsackievirus; Epstein-Barr virus; Hepatitis A virus; Hepatitis B virus; Hepatitis C virus; Herpes simplex virus, type 1; Herpes simplex virus, type 2; Cytomegalovirus; Human herpesvirus, type 8; Human immunodeficiency virus (HIV); Influenza virus; Measles virus; Mumps virus; Human papillomavirus; Parainfluenza virus; Poliovirus; Rabies virus; Respiratory syncytial virus; Rubella virus; and Varicella-zoster virus.

As used herein, the term "subject" refers to a non-plant species, including mammals or non-mammals, to which treatment with the compositions and compounds, according to the disclosure, can be administered. Mammalian species that can benefit from the disclosed methods of treatment include, but are not limited to, apes, chimpanzees, orangutans, humans, monkeys, and other animals such as dogs, cats, horses, cattle, pigs, sheep, goats, chickens, mice, rats, guinea pigs, and hamsters. In some embodiments, the subject is a human. The non-mammlian species include but are not limited to birds (e.g., chickens), fishes (e.g., tilapia, catfish, carp, salmon, and trout), shellfishes, shrimps, lobsters, prawns, bees (e.g., honey bees), and oysters. In one embodiment, the subject suffers from an infectious disease. In another embodiment, the subject is infected by a pathogen.

As used herein, the term "isolate" refers to a pure microbial culture separated from its natural origin, such as an isolate obtained by culturing a single microbial colony. An isolate is a pure culture derived from a heterogeneous, wild population of microorganisms.

As used herein, the term "strain" refers to an isolate or a group of isolates exhibiting phenotypic and/or genotypic traits belonging to the same lineage, distinct from those of other isolates or strains of the same species.

As used herein, the term "viral inhibitor" means any agents, compositions, compounds, biologics, and chemicals that can inhibit, suppress, and/or limit the functions, growth, or pathogenic activities of a virus.

As used herein, the term "culture medium" refers to all kinds of media which are used for culturing the microorganism, including but not limited to, a liquid broth and the remaining material when cells grown in the medium are removed, e.g., the supernatant remaining when cells grown in a liquid broth are removed by centrifugation, filtration, sedimentation, or other means well known in the art.

As used herein, the term "whole culture broth," "whole broth," or "WB" refers to a liquid culture of a microorganism in the culture medium, which may optionally include metabolites produced by the microorganism.

As used herein, the term "whole broth sterile filtrate," "sterile filtrate," or "SF" refers to liquid which is separated from the whole culture broth by use of a filter such that any intact bacterial cells are removed. The pore size of the filter varies, and can be determined by one of ordinary skill in the art. In some embodiments, the filter has a 0.22 micron pore size. In some embodiments, the pore size of the filter is less than 0.22 micron. In another embodiment, the pore size of the filter is greater than 0.22 micron.

As used herein, the term "BS3" means a culture medium comprising, or alternatively consisting essentially of, or yet further consisting of 5-20 g/L Soy peptone, 2-10 g/L Urea, 1-5 g/L CaCl$_2$, 2-10 g/L KH$_2$PO$_4$, 2-10 g/L K$_2$HPO$_4$, and 10-30 g/L Sucrose.

As used herein, the term "BS3-M2" means a culture medium comprising, or alternatively consisting essentially of, or yet further consisting of 5-20 g/L Soy peptone, 2-10 g/L Urea, 1-5 g/L CaCl$_2$, 2-10 g/L KH$_2$PO$_4$, 2-10 g/L K$_2$HPO$_4$, and 10-30 g/L Sucrose.

As used herein, the term "BS3-M9" means a culture medium comprising, or alternatively consisting essentially of, or yet further consisting of 5-20 g/L Low fat soy flour, 0.5-5 g/L CaCl$_2$, 4 g/L KH$_2$PO$_4$, 3.5 g/L K$_2$HPO$_4$, 10-30 g/L Sucrose, and 0.1-5 g/L ammonia sulfate.

As used herein, the term "BS3-M10" means a culture medium comprising, or alternatively consisting essentially of, or yet further consisting of 5-15 g/L Low fat soy flour, 2-10 g/L KH$_2$PO$_4$, 2-10 g/L K$_2$HPO$_4$, 10-30 g/L Sucrose, and 0.1-5 g/L ammonia sulfate.

As used herein, the term "GB6-M" means a culture medium comprising, or alternatively consisting essentially of, or yet further consisting of 5-40 g/L Maltrin® (M-180), 5-20 g/L Dextrose, 1-10 g/L yeast extract, 1-10 g/L Casein hydrolysate, and 0-5 g/L CaCO$_3$.

As used herein, the term "GB6-M3" means a culture medium comprising, or alternatively consisting essentially of, or yet further consisting of 10-30 g/L Maltrin® (M-250 or M-180), 5-20 g/L Dextrose, 2-10 g/L yeast extract, 2-10 g/L low fat soy flour, and 0.1-5 g/L CaCO$_3$.

As used herein, the term "GB6-M7" means a culture medium comprising, or alternatively consisting essentially of, or yet further consisting of 10-30 g/L Maltrin® (M-250 or M-180) 5-20 g/L Dextrose, 2-10 g/L yeast extract, 0.1-5 g/L ammonia sulfate, and 0.2-3 g/L CaCO$_3$.

As used herein, the term "GB6-M8" means a culture medium comprising, or alternatively consisting essentially of, or yet further consisting of 10-30 g/L Maltrin® (M-250 or M-180), 5-20 g/L Dextrose, 2-15 g/L yeast extract, 5-20 g/L low fat soy flour, 0.2-1.5 g/L ammonia sulfate, and 0.2-3 g/L CaCO$_3$.

As used herein, the term "GB6-M9" means a culture medium comprising, or alternatively consisting essentially of, or yet further consisting of 5-40 g/L Maltrin® (M-250 or M-180), 5-20 g/L Dextrose, 5-20 g/L low fat soy flour, and 0.2-5 g/L CaCO$_3$.

As used herein, the term "GB6-M10" means a culture medium comprising, or alternatively consisting essentially of, or yet further consisting of 5-40 g/L Maltrin® (M-250 or M-180), 5-25 g/l Dextrose, 1-10 g/L yeast extract, 1-10 g/L Low fat soy flour, 0.2-2 g/L ammonia sulfate, and 0-5 g/L CaCO$_3$.

As used herein, the term "GB6-M20" means a culture medium comprising, or alternatively consisting essentially of, or yet further consisting of 40-100 g/L Maltrin® (M-250 or M-180), 10-30 g/L Dextrose, 10-30 g/L yeast extract, 5-15 g/L low fat soy flour, 1-4 g/L ammonia sulfate, and 1-6 g/L CaCO$_3$.

As used herein, the term "GB6-M21" means a culture medium comprising, or alternatively consisting essentially of, or yet further consisting of 40-100 g/L Maltrin® (M-250 or M-180), 5-20 g/L Dextrose, 10-30 g/L yeast extract, 5-15 g/L low fat soy flour, 1-4 g/L ammonia sulfate, and 1-5 g/L CaCO$_3$.

As used herein, the term "GB6-M22" means a culture medium comprising, or alternatively consisting essentially of, or yet further consisting of 50-100 g/L Maltrin® (M-250 or M-180), 5-20 g/L Dextrose, 10-20 g/L yeast extract, 2-10 g/L low fat soy flour, 1-4 g/L ammonia sulfate, 1-4 g/L CaCO$_3$, and 0.1-1.5 ml/L antifoam.

As used herein, the term "GB6-M23" means a culture medium comprising, or alternatively consisting essentially of, or yet further consisting of 50-100 g/L Maltrin® (M-250 or M-180), 5-20 g/L Dextrose, 10-20 g/L yeast extract, 5-15 g/L low fat soy flour, 1-3 g/L ammonia sulfate, 1-4 g/L CaCO$_3$, and 0.1-1.2 ml/L antifoam.

As used herein, the term "GB6-M31" means a culture medium comprising, or alternatively consisting essentially of, or yet further consisting of 30-70 g/L Maltrin® (M-250 or M-180), 5-25 g/L dextrose, 5-15 g/L yeast, 2-10 g/L low fat soy flour, 0.5-3 g/L ammonia sulfate, 0.5-3 g/L CaCO$_3$, and 0.2-1.5 ml/L antifoam.

As used herein, the term "GB6-M33" means a culture medium comprising, or alternatively consisting essentially of, or yet further consisting of 50-100 g/L Maltrin® (M-250 or M-180), 5-25 g/L dextrose, 10-20 g/L yeast, 2-10 g/L low fat soy flour, 1-4 g/L ammonia sulfate, 1-5 g/L CaCO$_3$, and 0.2-1.5 ml/L antifoam.

As used herein, the term "GB6-M34" means a culture medium comprising, or alternatively consisting essentially of, or yet further consisting of 50-100 g/L Maltrin® (M-250 or M-180), 10-25 g/L dextrose, 1-10 g/L yeast, 2-10 g/L low fat soy flour, 1-4 g/L ammonia sulfate, 2-5 g/L CaCO$_3$, and 0.2-1 ml/L antifoam.

The term "carrier," in the present disclosure, refers to a substance linked with a pharmaceutical composition. In one embodiment, a carrier increases, decreases, or eliminates the physiological activity of the drug by binding to the drug. In another embodiment, a carrier is employed to minimize a decrease in the physiological activity of a drug of interest, linked to the carrier, while enhancing the in vivo stability of the drug. In another embodiment, the non-limiting examples of a carrier include diluent, adjuvant, excipient, or a vehicle with which the pharmaceutical composition is administered. Such pharmaceutical carriers can be sterile liquids, such as water and oils, including those of petroleum, animal, vegetable, or synthetic origin, such as peanut oil, soybean oil, mineral oil, sesame oil, and the like, polyethylene glycols, glycerin, propylene glycol, or other synthetic solvents. In some embodiments, water is a preferred carrier when the pharmaceutical composition is administered intravenously. Saline solutions and aqueous dextrose and glycerol solutions can also be employed as carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, propylene glycol, water, ethanol, and the like. The composition, if desired, can also contain minor amounts of wetting or emulsifying agents, or pH buffering agents such as acetates, citrates, or phosphates. In some embodiments, when the pharmaceutical composition is used topically, the carriers include, but are not limited to, reams, lotions, gels, emulsions, liposomes, aerosols, patches, poultices, subcutaneous depots, plasters, and sustained release systems designed to alter absorption kinetics in favor of zero order release.

As used herein, MS1479 refers to a bacterial strain deposited as ATCC Patent Deposit Designation No. PTA-124701, on Feb. 14, 2018.

As used herein, MS2379 refers to a bacterial strain deposited as ATCC® Patent Deposit Designation No. PTA-124703, on Feb. 14, 2018.

As used herein, MS2414 refers to a bacterial strain deposited as ATCC® Patent Deposit Designation No. PTA-124704, on Feb. 14, 2018.

As used herein, MS2820 refers to a bacterial strain deposited as ATCC® Patent Deposit Designation No. PTA-124710, on Feb. 14, 2018.

As used herein, MS0633 refers to a bacterial strain deposited as ATCC® Patent Deposit Designation No. PTA-124700, on Feb. 14, 2018.

As used herein, MS2335 refers to a bacterial strain deposited as ATCC® Patent Deposit Designation No. PTA-124702, on Feb. 14, 2018.

As used herein, MS2652 refers to a bacterial strain deposited as ATCC® Patent Deposit Designation No. PTA-124705, on Feb. 14, 2018.

As used herein, MS2658 refers to a bacterial strain deposited as ATCC® Patent Deposit Designation No. PTA-124706, on Feb. 14, 2018.

As used herein, MS2681 refers to a bacterial strain deposited as ATCC® Patent Deposit Designation No. PTA-124707, on Feb. 14, 2018.

As used herein, MS2697 refers to a bacterial strain deposited as ATCC® Patent Deposit Designation No. PTA-124708, on Feb. 14, 2018.

As used herein, MS2712 refers to a bacterial strain deposited as ATCC® Patent Deposit Designation No. PTA-124709, on Feb. 14, 2018.

As used herein, the term "metabolite" refers to any component, compound, substance, or byproduct produced by a microorganism, e.g., fungi and bacteria.

Bacterial Isolates and *Paenibacillus* Isolates

*Paenibacillus* species are facultative anaerobic, endospore-forming, gram-positive organisms previously included in the *Bacillus* genus. This disclosure provides newly-identified bacteria of *Paenibacillus* or *Bacillus*, which may exert multiple modes of actions (e.g., producing anti-microbial agents) to control pathogens or their related infectious diseases. In one embodiment, the *Paenibacillus* or *Bacillus* bacteria comprise, consist essentially of, or yet consist of MS1479, MS2379, MS2414, MS2820, MS0633, MS2335, MS2652, MS2658, MS2681, MS2697, or MS2712. It is contemplated that the disclosure is related to a composition for treating an infectious disease, where the composition comprises, consists essentially of, or yet consists of metabolites produced by a bacterium belonging to *Paenibacillus*. In one aspect, the bacterial isolate belongs to *Paenibacillus* spp. or *Paenibacillus polymyxa*. It is further contemplated that the composition comprises, or alternatively consists essentially of, or yet further consists of MS1479, MS2379, MS2414, or MS2820. The bacteria grows in a culture media comprising one or more of LB, TSB, BS3, BS3-M2, GB6-M3, GB6-M7, GB6-M8, GB6-M9, GB6-M22, GB6-M23, GB6-M10, GB6-M31, GB6-M33, and GB6-M34.

Thus, the disclosure provides a method of treating an infectious disease or a pathogen comprising administering an effective amount of composition, which comprises, consists essentially of, or yet consists of one or more of bacteria belonging to *Paenibacillus* or *Bacillus*. The bacteria comprise one or more of MS1479, MS2379, MS2414, MS2820, MS0633, MS2335, MS2652, MS2658, MS2681, MS2697, and MS2712. In another embodiment, the bacteria comprise one or both of MS2379 and MS2414. In some embodiments, the bacteria comprise one or more of MS1479, MS2379, MS2414, and MS2820.

The active agents produced by the *Paenibacillus* or *Bacillus* isolates demonstrate a broad spectrum of activities against pathogens, including but not limited to, bacteria, fungi, parasites, archaea, protists, viruses, prions (e.g., PrP$^{res}$ and PrP$^{se}$), microscopic plants (e.g., *Shewanella algae*, *Shewanella putrefaciens*, and *Shewanella xiamenensis*), and/or microscopic animals (e.g., plankton and planarian). In some embodiments, the viruses include, but are not limited to, RNA viruses such as flaviviruses, picornaviruses, rhabdoviruses, filoviruses, retroviruses (including lentiviruses), or DNA viruses such as adenoviruses, poxviruses, herpes viruses, cytomegaloviruses, hepadnaviruses, or others. In some embodiments, pathogens include bacteria, fungi, helminths, schistosomes, and trypanosomes. Other kinds of pathogens can include mammalian transposable elements.

The bacteria include, but are not limited to, "ESKAPE" pathogens *Enterococcus faecium*, *Staphylococcus aureus*, *Klebsiella pneumoniae*, *Acinetobacter baumannii*, *Pseudomonas aeruginosa*, and *Enterobacter* sp. In some embodiments, bacteria include, but are not limited to, *Actinomyces israelii*, *Bacillus anthracis*, *Bacteroides fragilis*, *Bordetella pertussis*, *B. burgdorferi*, *B. garinii*, *B. afzelii*, *B. abortus*, *B. canis*, *B. melitensis*, *B. suis*, *Campylobacter jejuni*, *C. trachomatis*, *C. pneumoniae*, *Chlamydophila psittaci*, *C. botulinum*, *C. difficile*, *C. perfringens*, *C. tetani*, *Corynebacterium diphtheriae*, *E. canis*, *E. chaffeensis*, *E. faecalis*, *E. faecium*, *E. coli*, Enterotoxigenic *E. coli* (ETEC), Enteropathogenic *E. coli*, Enteroinvasive *E. coli* (EIEC), Enterohemorrhagic *E. coli* (EHEC), *Francisella tularensis*, *Haemophilus influenzae*, *Helicobacter pylori*, *Klebsiella pneumoniae*, *Legionella pneumophila*, *Leptospira species*, *Listeria monocytogenes*, *M. leprae*, *M. tuberculosis*, *Mycoplasma pneumoniae*, *N. gonorrhoeae*, *N. meningitidis*, *Pseudomonas aeruginosa*, *Nocardia asteroides*, *Rickettsia rickettsii*, *Salmonella typhi*, *S. typhimurium*, *S. sonnei*, *S. dysenteriae*, *Staphylococcus aureus*, *Staphylococcus epidermidis*, *Staphylococcus saprophyticus*, *Streptococcus agalactiae*, *Streptococcus pneumoniae*, *Streptococcus pyogenes*, *Streptococcus viridans*, *Treponema pallidum*, *Vibrio cholerae*, and *Yersinia pestis*.

Non-limiting examples of fungi include *Absidia corymbifera* or *ramosa*, *Achorion gallinae*, *Actinomadura* spp., *Actinomyces* spp., *Ajellomyces dermatitidis*, *Aleurisma brasiliensis*, *Allescheria boydii*, *Arthroderma* spp., *Aspergillus* spp., *Basidiobolus* spp., *Blastomyces* spp., *Cadophora* spp., *Candida albicans*, *Cercospora apii*, *Chrysosporium* spp., *Cladosporium* spp., *Cladothrix asteroids*, *Coccidioides immitis*, *Cryptococcus neoformans*, *Cunninghamella elegans*, *Dematium wernecke*, *Discomyces israelii*, *Emmonsia* spp., *Emmonsiella capsulate*, *Endomyces geotrichum*, *Entomophthora coronata*, *Epidermophyton floccosum*, *Filobasidiella neoformans*, *Fonsecaea* spp., *Geotrichum candidum*, *Glenospora khartoumensis*, *Gymnoascus gypseus*, *Haplosporangium parvum*, *Histoplasma* spp., *Hormiscium dermatitidis*, *Hormodendrum* spp., *Keratinomyces* spp., *Langeronia soudanense*, *Leptosphaeria senegalensis*, *Lichtheimia corymbifera*, *Lobmyces loboi*, *Loboa loboi*, *Lobomycosis*, *Madurella* spp., *Malassezia furfur*, *Micrococcus pelletieri*, *Microsporum* spp. (ringworm), *Monilia* spp., *Mucor* spp., *Mycobacterium tuberculosis*, *Nannizzia* spp.,

*Neotestudina rosatii, Nocardia* spp., *Oidium albicans, Oospora lactis, Paracoccidioides brasiliensis, Petriellidium boydii, Phialophora* spp., *Piedraia hortae, Pityrosporum furfur, Pullularia gougerotii, Pyrenochaeta romeroi, Rhinosporidium seeberi, Sabouraudites (Microsporum), Sartorya fumigate, Sepedonium, Sporotrichum* spp., *Streptomyces* spp., *Tinea* spp. (ringworm), *Torula* spp., *Trichophyton* spp. (ringworm), *Trichosporon* spp., and *Zopfia rosatii*.

In some embodiments, the parasitic diseases include any conditions caused by a parasite. The parasites include, but are not limited to, endoparasites and ectoparasites. Non-limiting examples of parasites include Rafflesia, Cuscuta, Acanthocephala, Ascariasis (roundworms), Cestoda (tapeworms) including: *Taenia saginata* (human beef tapeworm), *Taenia solium* (human pork tapeworm), *Diphyllobothrium latum* (fish tapeworm) and Echinococcosis (hydatid tapeworm), *Clonorchis sinensis* (the Chinese liver fluke), *Dracunculus medinensis* (Guinea worm), *Enterobius vermicularis* (pinworm), Filariasis, Hookworm, *Loa loa*, Onchocerciasis (river blindness), Schistosomiasis, *Strongyloides stercoralis*, Tapeworm, *Toxocara canis* (dog roundworm), *Trichinella*, Whipworm, *Entamoeba histolytica, Entamoeba coli, Acanthamoeba, Balamuthia mandrillaris, Giardia, Cyclospora cayetanensis, Cryptosporidium, Toxoplasma gondii, Leishmania* (*L. tropica, L. donovani*, and *L. Mexicana*), *Plasmodium, Babesia, Gymnosporangium* and other rusts, *Pyrenophora teres, Cordyceps*, Arthropoda, Acari, *Varroa destructor, Cymothoa exigua*, Bed bugs, Culicidae (mosquitoes), Calyptra (vampire moths), Hippoboscoidea, Tsetse fly, Lipoptena, *Melophagus ovinus* (sheep keds) and relatives, Oestridae (bot flies), Human botfly, Phlebotominae (sand flies), Phthiraptera (Lice), Body louse, Crab louse, Head louse, Siphonaptera (fleas), Tabanidae (horse flies), Tantulocarida, Triatominae, Pea crab, Sacculina, Annelids, Hirudinea (some leeches), Monogeneans, *Calydiscoides euzeti, Lethacotyle vera, Protocotyle euzetmaillardi, Pseudorhabdosynochus* spp., Mollusks, *Cancellaria cooperii*, Glochidium, Pyramidellidae, Chordates, Cookiecutter shark, Candiru (vampire fish of Brazil, a facultative parasite), Lampreys, Deep sea anglers, False cleanerfish, Hood mockingbird, Oxpeckers, Snubnosed eel, Vampire bat, Vampire finch, Mistletoe, certain orchids, Corn smut, and certain mushrooms. In one embodiment, the parasites comprise *L. donovani, T. brucei*, and/or their worms at different life cycles.

Non-limiting examples of viruses include Adenovirus; Coxsackievirus; Epstein-Barr virus; Hepatitis A virus; Hepatitis B virus; Hepatitis C virus; Herpes simplex virus, type 1; Herpes simplex virus, type 2; Cytomegalovirus; Human herpesvirus, type 8; Human immunodeficiency virus (HIV); Influenza virus; Measles virus; Mumps virus; Human papillomavirus; Parainfluenza virus; Poliovirus; Rabies virus; Respiratory syncytial virus; Rubella virus; and Varicella-zoster virus.

Without being limited to a theory, the breadth of their anti-pathogen activities may be correlated to the bacterial isolates' unique genome sequences and secondary metabolite production, combined with their ability to establish sustained association with the subject in need thereof. In one aspect of the disclosure, with the optimized fermentation medium and process, the metabolites from isolates of *Paenibacillus* or *Bacillus* have shown increased efficacy against pathogens, both in vitro and in vivo.

All the *Paenibacillus* isolates MS1479, MS2379, MS2414, or MS2820 may control, suppress, or prevent the infectious diseases caused by pathogens, including viral, bacterial, and/or fungal pathogens.

Metabolites

Metabolites produced by microorganisms may also play a pivotal role in biodefense or biocontrol against the pathogens affecting a host or a subject. Microorganisms may produce two major types of metabolites-primary metabolites and secondary metabolites. Both types of metabolites may be associated with the biocontrol of pathogens in the host or subject. The secondary metabolites, which have no or limited effect on the life cycle of microorganisms, are often noted for their roles in interactions between organisms, for example, in biodefense against various pathogens, in toxicity of pathogens, or in attraction of beneficial organisms. See Hartmann, *Phytochemistry*, 68(22-24), 2831-2846 (2007). Thus, the secondary metabolites are often used as agonists against pathogens, e.g., pathogencides, pharmaceuticals, agrochemicals, food additives, or ingredients for cosmetics.

Fusaricidins are known for germicidal activity against plant pathogens, e.g., fungi (*Fusarium oxysporum, Aspergillusniger, Aspergillus oryzae* and *Pencilium thomii*). But the functions of fusaricidins against pathogens remain unexplored. Here, from the fermentation broth of *Paenibacillus* and *Bacillus* bacteria, Applicant identified 54 fusaricidins from MS2379 and MS2414, among which 37 Aare new fusaricidins. The identified fusaricidins are listed in Table 1, with their diagrammatic structures shown in FIG. 1. As such, fusaricidins of the claimed invention include all 54 fusaricidins as listed in Table 1.

TABLE 1

Fusaricidins identified from MS2379 and MS2414 extracts[a]

| No. | m/z(+) | Formula | FA.[b] | Amino acid in position | | | | | | RT[c] | Content[d] | Identification |
| --- | --- | --- | --- | --- | --- | --- | --- | --- | --- | --- | --- | --- |
| | | | | 1 | 2 | 3 | 4 | 5 | 6 | | | |
| Cyclic Insaricidin | | | | | | | | | | | | |
| 1 | 869.5445[e,f] | $C_{40}H_{72}N_{10}O_{11}$ | 15GHPD[g] | Thr | Val | Val | Ser | Asn | Ala | 12.09 | 1.4/2.3 | Fusaricidin $A_1$ |
| 2 | 869.5452 | $C_{40}H_{72}N_{10}O_{11}$ | 15GHPD | Ser | Val | Val | Thr | Asn | Ala | 10.82 | 1.6/1.6 | |
| 3 | 883.5606 | $C_{41}H_{74}N_{10}O_{11}$ | 15GHPD | Ser | Val | Val | Thr | Gln | Ala | 10.82 | 2.4/0.6 | |
| 4 | 883.5623[e] | $C_{41}H_{74}N_{10}O_{11}$ | 15GHPD | Thr | Val | Val | Ser | Gln | Ala | 12.09 | 2.5/0.8 | Fusaricidin $B_1$ |
| 5 | 883.5625[h] | $C_{41}H_{74}N_{10}O_{11}$ | 15GHPD | Thr | Val | Val | Thr | Asn | Ala | 13.41 | 27.0/28.6 | Fusaricidin A |
| 6 | 883.5600 | $C_{41}H_{74}N_{10}O_{11}$ | 15GHPD | Thr | Ile | Val | Ser | Asn | Ala | 14.61 | 0.1/0.5 | |
| 7 | 897.5777[h] | $C_{42}H_{76}N_{10}O_{11}$ | 15GHPD | Thr | Val | Val | Thr | Gln | Ala | 13.41 | 26.6/18.4 | Fusaricidin B |
| 8 | 897.5742 | $C_{42}H_{76}N_{10}O_{11}$ | 15GHPD | Thr | Ile | Val | Ser | Gln | Ala | 14.61 | 0.7/0.4 | |
| 9 | 897.5756[h] | $C_{42}H_{76}N_{10}O_{11}$ | 15GHPD | Thr | Val | Ile | Thr | Asn | Ala | 15.55 | 5.5/9.7 | LI-F05A |
| 10 | 897.576[h] | $C_{42}H_{76}N_{10}O_{11}$ | 15GHPD | Thr | Ile | Val | Thr | Asn | Ala | 15.89 | 3.2/6.2 | LI-F06A |
| 11 | 911.5927[h] | $C_{43}H_{78}N_{10}O_{11}$ | 15GHPD | Thr | Val | Ile | Thr | Gln | Ala | 15.55 | 7.0/5.2 | LI-F05B |
| 12 | 911.5940[h] | $C_{43}H_{78}N_{10}O_{11}$ | 15GHPD | Thr | Ile | Val | Thr | Gln | Ala | 15.89 | 3.4/3.7 | LI-F06B |

TABLE 1-continued

Fusaricidins identified from MS2379 and MS2414 extracts[a]

| No. | m/z(+) | Formula | FA.[b] | Amino acid in position 1 | 2 | 3 | 4 | 5 | 6 | RT[c] | Content[d] | Identification |
|---|---|---|---|---|---|---|---|---|---|---|---|---|
| 13 | 911.5932 | $C_{43}H_{78}N_{10}O_{11}$ | 15GHPD | Thr | Ile | Ile | Thr | Asn | Ala | 18.02 | 0.6/2.9 | LI-F08A |
| 14 | 911.5921 | $C_{43}H_{78}N_{10}O_{11}$ | 17GHHD[i] | Thr | Val | Val | Thr | Asn | Ala | 19.57 | 0.4/0.3 | |
| 15 | 925.6067[h] | $C_{44}H_{80}N_{10}O_{11}$ | 15GHPD | Thr | Ile | Ile | Thr | Gln | Ala | 18.02 | 0.8/1.5 | LI-F08B |
| 16 | 925.6070[f] | $C_{44}H_{80}N_{10}O_{11}$ | 17GHHD | Thr | Val | Val | Thr | Gln | Ala | 19.57 | 0.3/0.2 | |
| 17 | 925.6078 | $C_{44}H_{80}N_{10}O_{11}$ | 17GHHD | Thr | Val | Ile | Thr | Asn | Ala | 19.98 | 0.1/0.1 | |
| 18 | 931.5602[h] | $C_{45}H_{74}N_{10}O_{11}$ | 15GHPD | Thr | Val | Phe | Thr | Asn | Ala | 16.89 | 0.4/2.7 | LI-F07A |
| 19 | 933.5370 | $C_{44}H_{72}N_{10}O_{12}$ | 15GHPD | Thr | Val | Tyr | Ser | Asn | Ala | 10.65 | <0.1/0.2 | |
| 20 | 939.6203 | $C_{45}H_{82}N_{10}O_{11}$ | 17GHHD | Thr | Val | Ile | Thr | Gln | Ala | 19.98 | 0.1/0.1 | |
| 21 | 945.5772[h] | $C_{46}H_{76}N_{10}O_{11}$ | 15GHPD | Thr | Val | Phe | Thr | Gln | Ala | 16.89 | 0.6/1.4 | LI-F07B |
| 22 | 945.5735 | $C_{46}H_{76}N_{10}O_{11}$ | 15GHPD | Thr | Ile | Phe | Thr | Asn | Ala | 19.21 | <0.1/0.4 | |
| 23 | 947.5560 | $C_{45}H_{74}N_{10}O_{12}$ | 15GHPD | Thr | Val | Tyr | Ser | Gln | Ala | 10.65 | 0.2/<0.1 | |
| 24 | 947.5571[h] | $C_{45}H_{74}N_{10}O_{12}$ | 15GHPD | Thr | Val | Tyr | Thr | Asn | Ala | 11.20 | 2.4/6.1 | Fusaricidin C |
| 25 | 959.5908[f] | $C_{47}H_{78}N_{10}O_{11}$ | 15GHPD | Thr | Ile | Phe | Thr | Gln | Ala | 19.21 | 0.1/0.2 | |
| 26 | 961.5712[h] | $C_{46}H_{76}N_{10}O_{12}$ | 15GHPD | Thr | Val | Tyr | Thr | Gln | Ala | 11.20 | 3.1/2.2 | Fusaricidin D |
| 27 | 961.5722 | $C_{46}H_{76}N_{10}O_{12}$ | 15GHPD | Thr | Ile | Tyr | Thr | Asn | Ala | 12.91 | 0.3/1.8 | |
| 28 | 975.5868[f] | $C_{47}H_{78}N_{10}O_{12}$ | 15GHPD | Thr | Ile | Tyr | Thr | Gln | Ala | 12.91 | 0.3/0.6 | |
| Open-chain fusaricidin | | | | | | | | | | | | |
| 29 | 887.5546 | $C_{40}H_{74}N_{10}O_{12}$ | 15GHPD | Ser | Val | Val | Thr | Asn | Ala | 9.58 | 0.5/<0.1 | |
| 30 | 887.5594 | $C_{40}H_{74}N_{10}O_{12}$ | 15GHPD | Thr | Val | Val | Ser | Asn | Ala | 9.92 | 0.1/0.1 | |
| 31 | 901.5708 | $C_{41}H_{76}N_{10}O_{12}$ | 15GHPD | Ser | Val | Val | Thr | Gln | Ala | 9.58 | 0.5/<0.1 | |
| 32 | 901.5713 | $C_{41}H_{76}N_{10}O_{12}$ | 15GHPD | Thr | Val | Val | Ser | Gln | Ala | 9.92 | 0.2/<0.1 | |
| 33 | 901.5697[f] | $C_{41}H_{76}N_{10}O_{12}$ | 15GHPD | Thr | Val | Val | Thr | Asn | Ala | 10.32 | 1.6/0.4 | |
| 34 | 901.5737 | $C_{41}H_{76}N_{10}O_{12}$ | 15GHPD | Ser | Val | Val | Thr | Asn | GABA[j] | 10.65 | <0.1/0 | |
| 35 | 915.586[f] | $C_{42}H_{78}N_{10}O_{12}$ | 15GHPD | Thr | Val | Val | Thr | Gln | Ala | 10.32 | 3.6/0.2 | |
| 36 | 915.5899 | $C_{42}H_{78}N_{10}O_{12}$ | 15GHPD | Ser | Val | Val | Thr | Gln | GABA | 10.65 | <0.1/0 | |
| 37 | 915.5883 | $C_{42}H_{78}N_{10}O_{12}$ | 15GHPD | Thr | Val | Ile | Thr | Asn | Ala | 12.35 | 0.3/0.2 | |
| 38 | 915.5901 | $C_{42}H_{78}N_{10}O_{12}$ | 15GHPD | Thr | Val | Val | Thr | Asn | GABA | 12.05 | 0.6/0 | |
| 39 | 929.6045 | $C_{43}H_{80}N_{10}O_{12}$ | 15GHPD | Thr | Val | Ile | Thr | Gln | Ala | 12.35 | <0.1/0.1 | |
| 40 | 929.6028 | $C_{43}H_{80}N_{10}O_{12}$ | 15GHPD | Thr | Val | Val | Thr | Gln | GABA | 12.05 | 1.2/0 | |
| 41 | 929.6045 | $C_{43}H_{80}N_{10}O_{12}$ | 15GHPD | Thr | Val | Ile | Thr | Asn | GABA | 14.04 | <0.1/<0.1 | |
| 42 | 935.5560 | $C_{44}H_{74}N_{10}O_{12}$ | 15GHPD | Thr | Val | Phe | Ser | Asn | Ala | 13.25 | 0/<0.1 | |
| 43 | 943.6185 | $C_{44}H_{82}N_{10}O_{12}$ | 15GHPD | Thr | Ile | Val | Thr | Gln | GABA | 13.95 | <0.1/0 | |
| 44 | 943.6220 | $C_{44}H_{82}N_{10}O_{12}$ | 15GHPD | Thr | Val | Ile | Thr | Gln | GABA | 14.04 | 0.1/<0.1 | |
| 45 | 949.5717 | $C_{45}H_{76}N_{10}O_{12}$ | 15GHPD | Thr | Val | Phe | Thr | Asn | Ala | 14.18 | 0/<0.1 | |
| 46 | 949.5717 | $C_{45}H_{76}N_{10}O_{12}$ | 15GHPD | Thr | Val | Phe | Ser | Gln | Ala | 13.25 | 0/<0.1 | |
| 47 | 951.5510 | $C_{44}H_{74}N_{10}O_{13}$ | 15GHPD | Ser | Val | Tyr | Thr | Asn | Ala | 7.65 | 0/<0.1 | |
| 48 | 951.5510 | $C_{44}H_{74}N_{10}O_{13}$ | 15GHPD | Thr | Val | Tyr | Thr | Asn | Gly | 8.27 | 0/<0.1 | |
| 49 | 957.6350 | $C_{45}H_{84}N_{10}O_{12}$ | 15GHPD | Thr | Ile | Ile | Thr | Gln | GABA | 16.11 | <0.1/0 | |
| 50 | 963.5873 | $C_{46}H_{78}N_{10}O_{12}$ | 15GHPD | Thr | Val | Phe | Thr | Gln | Ala | 14.18 | 0/<0.1 | |
| 51 | 965.5666 | $C_{45}H_{76}N_{10}O_{13}$ | 15GHPD | Ser | Val | Tyr | Thr | Gln | Ala | 7.65 | 0/<0.1 | |
| 52 | 965.5666 | $C_{45}H_{76}N_{10}O_{13}$ | 15GHPD | Thr | Val | Tyr | Thr | Gln | Gly | 8.27 | 0/<0.1 | |
| 53 | 965.5661 | $C_{45}H_{76}N_{10}O_{13}$ | 15GHPD | Thr | Val | Tyr | Thr | Asn | Ala | 8.71 | 0.2/<0.1 | |
| 54 | 979.5832 | $C_{46}H_{78}N_{10}O_{13}$ | 15GHPD | Thr | Val | Tyr | Thr | Gln | Ala | 8.71 | 0.3/<0.1 | |

[a]A total of 54 fusaricidins were idenfied from MS2414, among which 43 were identified from MS2379.
[b]Fatty acid side chain.
[c]Retention time (min);
[d]Relative content (%) in the total extract of MS2379/MS2414.
[e]Isolated from MS2379.
[f]Detected previously by LC-MS.
[g]5-Guanidino-3-hydroxypentadecanoic acid.
[h]Isolated from other microbial strains and its structure unequivocally determined.
[i]17-Guanidino-3-hydroxyheptadecanoic acid.
[j]γ-aminobutyric acid.

In sum, two types of fusaricidins were identified from the fermentation broth-cyclic fusaricidins and open-end fusaricidins. The identified cyclic fusaricidins have a ring structure with six amino acid residues at different positions, wherein the ring structure has a 15-guanidino-3-hydroxypentadecanoyl (GHPD) side chain or 17-guanidino-3-(R)-hydroxyheptadecanoyl (GHHD) side chain. In one embodiment, the cyclic fusaricidin is a compound of Formula I:

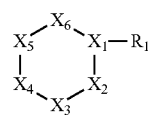

Formula I wherein $X_1$ is Thr or Ser; $X_2$ is Val or Ile; $X_3$ is selected from a group consisting of Val, Ile, Tyr, and Phe; $X_4$ is Thr or Ser; $X_5$ is Asn or Gln; $X_6$ is Ala; wherein $R_1$ is a 15-guanidino-3-hydroxypentadecanoyl (GHPD) side chain or 17-guanidino-3-(R)-hydroxyheptadecanoyl (GHHD) side chain. For example, fusaricidin $A_1$(No. 1 fusaricidin in Table 1) has a formula of $C_{40}H_{72}N_{10}O_{11}$ and a GHPD side chain. On the amino acid ring of fusaricidin $A_1$, Thr is at the position 1, Val at position 2, Val at position 3, Ser at position 4, Asn at position 5, and Ala at position 6. On the ring structure of fusaricidin $B_1$, Thr is at the position 1, Val at position 2, Val at position 3, Ser at position 4, Gln at position 5, and Ala at position 6. On the ring structure of fusaricidin A, Thr is at the position 1, Val at position 2, Val at position 3, Thr at position 4, Asn at position 5, and Ala at position 6. On the ring structure of fusaricidin B, Thr is at the position 1, Val at position 2, Val at position 3, Thr at position 4, Gln at position 5, and Ala at position 6. All of the fusaricidins A, B, $A_1$ and $B_1$ have a GHPD side chain (Table 1). Formula I only depicts the relative positions of amino acids and the side chain and does not define the conformation and bond angles.

The amino acids on Forma I can be either a D-amino acid or an L-amino acid. An amide bond attaches the carbonyl moiety of $R_1$ to the amino group of $X_1$, the carbonyl group of $X_1$ to the amino group of $X_2$, the carbonyl moiety of $X_2$ to the amino group of $X_3$, the carbonyl moiety of $X_3$ to the amino group of $X_4$, the carbonyl moiety of $X_4$ to the amino group of $X_5$, and the carbonyl moiety of $X_5$ to the amino group of $X_6$. An ester bond attaches the carbonyl group of $X_6$ to the hydroxyl group of $X_1$.

In one embodiment, in the cyclic fusaricidin, $X_1$ is Thr; $X_2$ is Val; $X_3$ is Val; $X_4$ is Thr or Ser; $X_5$ is Asn; wherein $R_1$ is a GHPD side chain. In another embodiment, the cyclic fusaricidin comprises one or both of fusaricidin $A_1$ and fusaricidin A. In another embodiment, in the cyclic fusaricidin $X_1$ is Thr; $X_2$ is Val; $X_3$ is Val; $X_4$ is Thr or Ser; $X_5$ is Gln; wherein $R_1$ is a GHPD side chain. In one embodiment, $X_1$ is L-Thr; $X_2$ is D-Val; $X_3$ is L-Val; $X_4$ is D-allo-Thr; $X_5$ is D-Asn and $X_6$ is D-Ala. In another embodiment, $X_1$ is L-Thr; $X_2$ is D-Val; $X_3$ is L-Val; $X_4$ is D-allo-Thr; $X_5$ is D-Gln and $X_6$ is D-Ala. The cyclic fusaricidin, in some embodiments, comprises one or both of fusaricidin $B_1$ and fusaricidin B.

The open-chain fusaricidins also comprise six amino acid residues, which do not form a ring structure. The open-end fusaricidins also comprise a GHPD side chain. In one embodiment, the open-chain fusaricidin is a compound of Formula II:

Formula II wherein $X_7$ is Thr or Ser; $X_8$ is Val or Ile; $X_9$ is selected from a group consisting of Val, Ile, Tyr, and Phe; $X_{10}$ is Thr or Ser; $X_{11}$ is Asn or Gln; $X_{12}$ is selected from a group consisting of Ala, GABA, and Gly; wherein $R_1$ is a GHPD side chain. For example, No. 29 fusaricidin has a formula of $C_{40}H_{74}N_{10}O_{12}$ and a GHPD side chain. On the amino acid chain of fusaricidin No. 29, Ser is at the position 7, Val at position 8, Val at position 9, Thr at position 10, Asn at position 11, and Ala at position 12 (Table 1).

The amino acids on Forma II can be either a D-amino acid or an L-amino acid. Formula II only depicts the relative positions of amino acids and the side chain and does not define the confirmation and bond angles. An amide bond attaches the carbonyl moiety of $R_1$ to the amino group of $X_7$, the carbonyl group of $X_7$ to the amino group of $X_8$, the carbonyl moiety of $X_8$ to the amino group of $X_9$, the carbonyl moiety of $X_9$ to the amino group of $X_{10}$, the carbonyl moiety of $X_{10}$ to the amino group of $X_{11}$, and the carbonyl moiety of $X_{11}$ to the amino group of $X_{12}$.

Thus, the disclosure also provides a composition comprising, consisting essentially of, or yet consisting of a fusaricidin that is a compound of Formula I or Formula II. In one embodiment, the fusaricidin comprises one or more of the fusaricidins as disclosed in Table 1. The fusaricidin is produced by a bacterium of *Paenibacillus* and/or *Bacillus* as a metabolite or is synthesized independent of the *Paenibacillus* and *Bacillus* bacteria. In one aspect of the invention, the bacterium that produces fusaricidins belongs to *Paenibacillus polymyxa* or *Paenibacillus* spp. In one embodiment, the bacteria comprise, or alternatively consist essentially of, or yet further consist of one or more of MS1479, MS2379, MS2414, MS2820, MS0633, MS2335, MS2652, MS2658, MS2681, MS2697, or MS2712. In another aspect, the bacteria comprise, or alternatively consist essentially of, or yet further consist of MS1479, MS2379, MS2414, or MS2820. In yet another embodiment, the fusaricidin or the bacterial metabolites may be present in the whole culture broth, fermentation broths, the supernatant, or the cell pellets, or may be bound to the bacterial membranes.

The fusaricidins are extracted for further analysis, e.g., liquid chromatography-mass spectrometry (LC-MS) analysis. The fermentation broths of the bacteria are extracted by methods well known in the art. The non-limiting examples of suitable solvents for extraction include n-butanol (n-BuOH), chloroform, methanol (MeOH), ethyl acetate, ethyl ether, and tetrahydrofuran. Selection of the solvent is not believed to be critical to practice of the invention, and solvents other than those set forth can be employed, especially solvents having polarity similar to those described above. In one embodiment, the solvent used for extracting fermentation broth is chloroform, n-butanol, and/or methanol.

In one exemplary extraction, 3 mL of MeOH is added to 7.5 mL of broth of one or more of MS1479, MS2379, MS2414, MS2820, MS0633, MS2335, MS2652, MS2658, MS2681, MS2697, and MS2712, and the mixture is sonicated for 15 mins. Then, $CHCl_3$ (10 mL) is added to the mixture and sonicated again for 10 min. The mixture is transferred to a separatory funnel, followed by shaking and separation of organic layer from aqueous layer. The $CHCl_3$ phase is withdrawn. The organic solvent is removed by rotary evaporation, and the concentrate was transferred by syringe, through a 0.25µ membrane filter, into a tared, labeled vial. After high vacuum drying, the weight of the organic extract is recorded. The samples processed by this protocol and the resultant extracts were analyzed by LC-MS and TLC.

In another embodiment, during the extraction, the sample (e.g., fermentation broth of MS2414 in GB6-M medium or MS2414 in BS3-M2 medium) is centrifuged at room temperature for 30 min at 3000 rpm. The relatively clear supernatants are extracted with n-BuOH (situated with water) to afford the n-BuOH extracts. In one embodiment, 25 mL of the supernatant is extracted with 20 mL of n-BuOH (situated with water) to afford the following n-BuOH extracts. Cell pellets (with a small amount of medium) from MS2414 in GB6-M were extracted with 90% MeOH to afford the MeOH extract. Cell pellets (with a small amount of medium) from MS2414 in BS3-M2 are extracted with 90% MeOH to afford a MeOH extract.

Both n-BuOH and MeOH extracts are analyzed by LC-MS and TLC. All eight samples of the extracts were analyzed by LC-MS (Table 2).

TABLE 2

| LC-MS method and instrument setup & conditions for analysis | |
|---|---|
| HPLC | Agilent HPLC 1100 Series |
| Column | Agilent Poroshell 120 EC-C18 2.7 μm, 2.1 × 150 mm |
| Mobile Phase | Water (A) + Acetonitrile (B), both containing 0.1% Formic acid (Gradient) |
| Flow Rate | 0.23 mL/min |
| Run time | 25 min |
| Injection Volume/s | 1 μL |
| TOF-MS | Agilent TOF-MS 6200 series |
| Ionization mode | ESI+ |
| Gas temperature | 300° C. |
| Gas Flow | 10 L/min |
| Nebulizer | 30 psig |
| Capillary voltage | 3.5 kV |
| Fragmentor | 125 V |
| Mass Range (m/z) | 100-1500 |

The production of metabolites from the bacterial isolates may also depend on the certain medium and the volume of fermentation broth used in culturing the bacterial isolates. In one embodiment, the medium modifications, e.g., LB, TSB, BS3, BS3-M2, GB6-M3, GB6-M7, GB6-M8, GB6-M9, GB6-M22, GB6-M23, GB6-M10, GB6-M31, GB6-M33, and GB6-M34, may increase or reduce the production of the metabolites, including but not limited to, the fusaricidin-type compounds. In another embodiment, the media modifications may alter, enhance, or reduce the predominance of the metabolites, including but not limited to, the fusaricidin-type compounds. In some embodiments, the volumes of fermentation for culturing the bacterial isolates ranges from less than 1 ml, from 1 ml to 100 ml, from 100 ml to 500 ml, from 500 ml to 1 L, from 1 L to 5 L, from 5 L to 20 L, from 20 L to 50 L, from 50 L to 100 L, from 100 L to 1,000 L, or more than 1,000 L. In one aspect, the disclosure provides a method of producing a fusaricin, comprising culturing a bacterium of *Paenibacillus* or *Bacillus* species in a production medium. In one embodiment, the bacterium comprises one or more of MS1479, MS2379, MS2414, MS2820, MS0633, MS2335, MS2652, MS2658, MS2681, MS2697, and MS2712. In another embodiment, the bacterium is one or both of MS2379 and MS2414. In one embodiment, the production medium comprises one or more of LB, TSB, BS3, BS3-M2, GB6-M3, GB6-M7, GB6-M8, GB6-M9, GB6-M22, GB6-M23, GB6-M10, GB6-M31, GB6-M33, and GB6-M34. The fusaricidin produced by this method is a cyclic fusaricidin or an open-chain fusaricidin. In one embodiment, the cyclic fusaricidin is a compound of Formula I, wherein $X_1$ is Thr or Ser; $X_2$ is Val or Ile; $X_3$ is selected from a group consisting of Val, Ile, Tyr, and Phe; $X_4$ is Thr or Ser; $X_5$ is Asn or Gln; $X_6$ is Ala; wherein $R_1$ is a 15-guanidino-3-hydroxypentadecanoyl (GHPD) side chain or 17-guanidino-3-(R)-hydroxyheptadecanoyl (GHHD) side chain. In one embodiment, the open-chain fusaricidin is a compound of Formula II, wherein $X_7$ is Thr or Ser; $X_8$ is Val or Ile; $X_9$ is selected from a group consisting of Val, Ile, Tyr, and Phe; $X_{10}$ is Thr or Ser; $X_{11}$ is Asn or Gln; $X_{12}$ is selected from a group consisting of Ala, GABA, and Gly; wherein $R_1$ is a GHPD side chain.

Surprisingly, Applicant discovered the anti-pathogen activities from newly identified bacterial strains (*Paenibacillus* and *Bacillus*), and their fermentation broth and metabolites. For example, *Paenibacillus* strains demonstrated their efficacy against the ESKAPE pathogens with MS2379 showing strong inhibitory activity against the two gram-positive bacteria (*E. faecium* and *S. aureus*) (Table 6). Further, both the fermentation media and the column fractions from the extract of MS2414 also showed strong anti-microbial activities against several pathogens, e.g., *Candida albicans, Candida glabrata, Candida krusei, Aspergillus fumigatus, Cryptococcus neoformans, Staphylococcus aureus*, MRSA, *Escherichia coli, Pseudomonas aeruginosa*, and *Mycobacterium intracellulare* (FIG. 6). Particularly, column fractions 131-135 and 136-152 of MS2414 extracts, n-BuOH and MeOH extracts of MS2414 showed antifungal activities that are comparable to commercial antifungal agents, e.g., Amphotericin B. Notably, the column fractions demonstrated more potent antifungal effects against *C. neoformans* than Amphotericin B. Without being bound by a theory, the specific fractions or the active ingredients within the column fractions may exert the anti-microbial effects from the fermentation broth.

Unexpectedly, the LC-MS data identified the abundance of various fusaricidins in the fermentation broths (Table 10). Further studies confirmed the anti-microbial activities of the isolated fusaricidins, even against antibiotics-resistant pathogens (Table 13). Fusaricidins are contained in both supernatant and cell pellets. Due to the polar arginine residue, fusaricidins are slightly soluble in water, but are more likely present in the cell pellets. Without being bound by a theory, less presence of fusaricidins in the supernatant than the cell pellets may explain the weak in-vitro control of *Pythium* by the sterile filtrate of supernatant.

Thus, in another aspect, the present invention provides a method for treating an infectious disease or a pathogen in a subject, comprising administering to the subject an effective amount of a fusaricidin. The fusaricidin of this disclosure comprises one or more of those listed in Table 1. It can be a cyclic fusaricidin or an open-ended fusaricidin. In one embodiment, the cyclic fusaricidin is a compound of Formula I, wherein $X_1$ is Thr or Ser; $X_2$ is Val or Ile; $X_3$ is selected from a group consisting of Val, Ile, Tyr, and Phe; $X_4$ is Thr or Ser; $X_5$ is Asn or Gln; $X_6$ is Ala; wherein $R_1$ is a 15-guanidino-3-hydroxypentadecanoyl (GHPD) side chain or 17-guanidino-3-(R)-hydroxyheptadecanoyl (GHD) side chain. In another embodiment, $X_1$ is Thr; $X_2$ is Val; $X_3$ is Val; $X_4$ is Thr or Ser; $X_5$ is Asn; wherein $R_1$ is a GHPD side chain on Formula I. In another embodiment, $X_1$ is Thr; $X_2$ is Val; $X_3$ is Val; $X_4$ is Thr or Ser; $X_5$ is Gln; wherein $R_1$ is a GHPD side chain on the Formula I. The cyclic fusaricidin comprises one or more of fusaricidin $A_1$, fusaricidin A, fusaricidin $B_1$ and fusaricidin B. The open-chain fusaricidin is a compound of Formula II: wherein $X_7$ is Thr or Ser; $X_8$ is Val or Ile; $X_9$ is selected from a group consisting of Val, Ile, Tyr, and Phe; $X_{10}$ is Thr or Ser; $X_{11}$ is Asn or Gln; $X_{12}$ is selected from a group consisting of Ala, GABA, and Gly; wherein $R_1$ is a GHPD side chain.

The fusaricidin can be produced by a bacterium of *Paenibacillus* or *Bacillus* species, or synthesized. Thus, in another aspect, the disclosure is also directed to a method of treating an infectious disease or a pathogen in a subject, comprising administering to the subject an effective amount of a *Paenibacillus* and/or *Bacillus* bacterium. The bacterium comprises one or more of MS1479, MS2379, MS2414, MS2820, MS0633, MS2335, MS2652, MS2658, MS2681, MS2697, and MS2712. In one embodiment, the bacterium is one or both of MS2379 and MS2414. In one embodiment, the subject is a mammal or a non-mammal. The subject is a human, in one embodiment.

The methods of this disclosure can be used for treatment various pathogens, including bacteria, fungi, archaea (e.g., methanogens, halophiles, thermophiles, and psychrophiles), parasites, protists, viruses, and prions. In one embodiment, the pathogen is a bacterium, a fungus, a virus, or a parasite.

The bacteria that can be treated by the method include but are not limited to "ESKAPE" pathogens *Enterococcus faecium*, *Staphylococcus aureus*, *Klebsiella pneumoniae*, *Acinetobacter baumannii*, *Pseudomonas aeruginosa*, and *Enterobacter* sp. In some embodiments, bacteria include, but are not limited to, *Actinomyces israelii*, *Bacillus anthracis*, *Bacteroides fragilis*, *Bordetella pertussis*, *B. burgdorferi*, *B. garinii*, *B. afzelii*, *B. abortus*, *B. canis*, *B. melitensis*, *B. suis*, *Campylobacter jejuni*, *C. trachomatis*, *C. pneumoniae*, *Chlamydophila psittaci*, *C. botulinum*, *C. difficile*, *C. perfringens*, *C. tetani*, *Corynebacterium diphtheriae*, *E. canis*, *E. chaffeensis*, *E. faecalis*, *E. faecium*, *E. coli*, Enterotoxigenic *E. coli* (ETEC), Enteropathogenic *E. coli*, Enteroinvasive *E. coli* (EIEC), Enterohemorrhagic *E. coli* (EHEC), *Francisella tularensis*, *Haemophilus influenzae*, *Helicobacter pylori*, *Klebsiella pneumoniae*, *Legionella pneumophila*, *Leptospira species*, *Listeria monocytogenes*, *M. leprae*, *M. tuberculosis*, *Mycoplasma pneumoniae*, *N. gonorrhoeae*, *N. meningitidis*, *Pseudomonas aeruginosa*, *Nocardia asteroides*, *Rickettsia rickettsii*, *Salmonella typhi*, *S. typhimurium*, *S. sonnei*, *S. dysenteriae*, *Staphylococcus aureus*, *Staphylococcus epidermidis*, *Staphylococcus saprophyticus*, *Streptococcus agalactiae*, *Streptococcus pneumoniae*, *Streptococcus pyogenes*, *Streptococcus viridans*, *Treponema pallidum*, *Vibrio cholerae*, and *Yersinia pestis*. In another embodiment, the bacterium comprises one or more of *S. aureus*, *E. faecium*, *E. coli*, and *P. aeruginosa*.

In another embodiment, the method of this disclosure can treat fungi, which include *Absidia corymbifera* or *ramosa*, *Achorion gallinae*, Actinomadura spp., Actinomyces spp., *Ajellomyces dermatitidis*, *Aleurisma brasiliensis*, *Allescheria boydii*, Arthroderma spp., Aspergillus spp., Basidiobolus spp., Blastomyces spp., Cadophora spp., *Candida albicans*, Cercospora apii, Chrysosporium spp., Cladosporium spp., *Cladothrix asteroids*, *Coccidioides immitis*, *Cryptococcus neoformans*, *Cunninghamella elegans*, *Dematium wernecke*, *Discomyces israelii*, Emmonsia spp., *Emmonsiella capsulate*, *Endomyces geotrichum*, *Entomophthora coronata*, *Epidermophyton floccosum*, *Filobasidiella neoformans*, Fonsecaea spp., *Geotrichum candidum*, *Glenospora khartoumensis*, *Gymnoascus gypseus*, *Haplosporangium parvum*, Histoplasma spp., *Hormiscium dermatitidis*, Hormodendrum spp., Keratinomyces spp., *Langeronia soudanense*, *Leptosphaeria senegalensis*, *Lichtheimia corymbifera*, *Lobmyces loboi*, *Loboa loboi*, *Lobomycosis*, Madurella spp., *Malassezia furfur*, *Micrococcus pelletieri*, Microsporum spp. (ringworm), Monilia spp., Mucor spp., *Mycobacterium tuberculosis*, Nannizzia spp., *Neotestudina rosati*, Nocardia spp., *Oidium albicans*, *Oospora lactis*, *Paracoccidioides brasiliensis*, *Petriellidium boydii*, Phialophora spp., *Piedraia hortae*, *Pityrosporum furfur*, *Pullularia gougerotii*, *Pyrenochaeta romeroi*, *Rhinosporidium seeberi*, *Sabouraudites* (*Microsporum*), *Sartorya fumigate*, Sepedonium, Sporotrichum spp., Streptomyces spp., Tinea spp. (ringworm), Torula spp., Trichophyton spp. (ringworm), Trichosporon spp., and *Zopfia rosatii*. In another embodiment, the fungus comprises one or more of *C. neoformans*, *C. albicans*, and *A. fumigatus*.

The pathogens include those that are resistant to or less effectivity to be treated by traditional treatments. In one embodiment, *S. aureus* is methicillin-resistant. In another embodiment, *E. faecium* is vancomycin-resistant.

In some embodiments, the method is used to treat parasites. The parasites, in some embodiments, include endoparasites and ectoparasites. In one embodiment, Rafflesia, Cuscuta, Acanthocephala, Ascariasis (roundworms), Cestoda (tapeworms) including: *Taenia saginata* (human beef tapeworm), *Taenia solium* (human pork tapeworm), *Diphyllobothrium latum* (fish tapeworm) and Echinococcosis (hydatid tapeworm), *Clonorchis sinensis* (the Chinese liver fluke), *Dracunculus medinensis* (Guinea worm), *Enterobius vermicularis* (pinworm), Filariasis, Hookworm, *Loa loa*, Onchocerciasis (river blindness), Schistosomiasis, *Strongyloides stercoralis*, Tapeworm, *Toxocara canis* (dog roundworm), *Trichinella*, Whipworm, *Entamoeba histolytica*, *Entamoeba coli*, Acanthamoeba, *Balamuthia mandrillaris*, Giardia, *Cyclospora cayetanensis*, Cryptosporidium, *Toxoplasma gondii*, Leishmania (*L. tropica*, *L. donovani*, and *L. Mexicana*), Plasmodium, Babesia, Gymnosporangium and other rusts, *Pyrenophora teres*, Cordyceps, Arthropoda, Acari, *Varroa destructor*, *Cymothoa exigua*, Bed bugs, Culicidae (mosquitoes), Calyptra (vampire moths), Hippoboscoidea, Tsetse fly, Lipoptena, *Melophagus ovinus* (sheep keds) and relatives, Oestridae (bot flies), Human botfly, Phlebotominae (sand flies), Phthiraptera (Lice), Body louse, Crab louse, Head louse, Siphonaptera (fleas), Tabanidae (horse flies), Tantulocarida, Triatominae, Pea crab, Sacculina, Annelids, Hirudinea (some leeches), Monogeneans, *Calydiscoides euzeti*, *Lethacotyle vera*, *Protocotyle euzetmaillardi*, Pseudorhabdosynochus spp., Mollusks, *Cancellaria cooperii*, Glochidium, Pyramidellidae, Chordates, Cookiecutter shark, Candiru (vampire fish of Brazil, a facultative parasite), Lampreys, Deep sea anglers, False cleanerfish, Hood mockingbird, Oxpeckers, Snubnosed eel, Vampire bat, Vampire finch, Mistletoe, certain orchids, Corn smut, and certain mushrooms. In some embodiments, the parasite is *L. donovani* or *T. brucei*, and/or their worms at different life cycles (e.g., promastigote and amastigote).

Combination Treatment

The method of treating infectious diseases or inhibiting the pathogens may further comprise, or alternatively consist essentially of, or yet further consist of the addition of antibiotics for combination or synergistic therapy. The appropriate antibiotic administered will typically depend on the susceptibility of the pathogen. For example, gram-negative or gram-positive bacteria may respond to different antibiotics. The suitable types of antibiotics are easily discernable by one of skill in the art.

The method of inhibiting the growth of pathogens (e.g., bacteria) may further include the addition of antibiotics for combination or synergistic therapy. Examples of particular classes of antibiotics useful for synergistic or combination therapy with the active ingredients of the disclosure include aminoglycosides (e.g., tobramycin), penicillins (e.g., piperacillin), cephalosporins (e.g., ceftazidime), fluoroquinolones (e.g., ciprofloxacin), carbapenems (e.g., imipenem), tetracyclines, and macrolides (e.g., erythromycin and clarithromycin). The appropriate antibiotic administered will typically depend on the susceptibility of the bacteria, such as whether the bacteria is gram-negative or gram-positive, and will be easily discernable by one of skill in the art. Non-limiting examples of antibiotics include aminoglycosides (amikacin, gentamicin, kanamycin, netilmicin, tobramycin, streptomycin, azithromycin, clarithromycin, erythromycin, erythromycin estolate/ethylsuccinate/gluceptate/lactobionate/stearate), beta-lactams such as penicillins (e.g., penicillin G, penicillin V, methicillin, nafcillin, oxacillin, cloxacillin, dicloxacillin, ampicillin, amoxicillin, ticarcillin, carbenicillin, mezlocillin, azlocillin and piperacillin), or cephalosporins (e.g., cephalothin, cefazolin, cefaclor, cefamandole, cefoxitin, cefuroxime, cefonicid, cefmetazole, cefotetan, cefprozil, loracarbef, cefetamet, cefoperazone, cefotaxime, ceftizoxime, ceftriaxone, ceftazidime, cefepime, cefixime, cefpodoxime, and cefsulodin). Other classes of antibiotics include, but are not limited to, carbapenems (e.g., imipenem), monobactams (e.g., aztreonam), quinolones (e.g., fleroxacin, nalidixic acid, norfloxacin, ciprofloxacin, ofloxacin, enoxacin, lomefloxacin and cinoxacin), tetracyclines (e.g., doxycycline, minocycline, tetracycline), and glycopeptides (e.g., vancomycin, teicoplanin), for example. In some embodiments, antibiotics include but are not limited to chloramphenicol, clindamycin, trimethoprim, sulfamethoxazole, nitrofurantoin, rifampin, and mupirocin.

It will be readily understood by those skilled in the art that any suitable pharmaceutically acceptable liposome may be used as a vehicle for the composition of the present invention. Such liposomal compositions have activity against many microorganisms similar to the activity of other compositions of this invention discussed in more detail above. Additionally, these compositions may be administered in a variety of conventional and well-known ways as is also discussed in greater detail above.

Pharmaceutically acceptable carrier preparations for administration comprise, or alternatively consist essentially of, or yet further consist of sterile or aqueous or non-aqueous solutions, suspensions, and emulsions. Non-limiting examples of non-aqueous solvents are propylene glycol, polyethylene glycol, vegetable oils such as olive oil, and injectable organic esters such as ethyl oleate. Non-limiting examples of aqueous carriers include water, alcoholic/aqueous solutions, emulsions, or suspensions, including saline and buffered media. Non-limiting examples of parenteral vehicles include sodium chloride solution, Ringer's dextrose, dextrose and sodium chloride, lactated Ringer's, or fixed oils. An active agent or therapeutic ingredient is often mixed with excipients that are pharmaceutically acceptable and compatible with the active ingredient. Non-limiting examples of suitable excipients include water, saline, dextrose, glycerol, and ethanol, or combinations thereof. Intravenous vehicles include, but are not limited to, fluid and nutrient replenishers, electrolyte replenishers such as those based on Ringer's dextrose, and the like. Preservatives and other additives may also be present, such as, for example, antimicrobials, antioxidants, chelating agents, inert gases, and the like.

Another therapeutic approach included within the invention involves direct administration of reagents or compositions by any conventional administration techniques (for example, but not restricted to, local injection, inhalation, or administered systemically), to the subject with a microbial, bacterial, viral, or fungal disorder. The reagent, formulation, or composition may also be targeted to specific cells or receptors by any of the methods described herein. The actual dosage of reagent, formulation, or composition that modulates a microbial, bacterial, viral, or fungal disorder depends on many factors, including the size and health of an organism. However, one of ordinary skill in the art can use the following teachings describing the methods and techniques for determining clinical dosages to determine the appropriate dosage to use: Spilker B., *Guide to Clinical Studies and Developing Protocols*, Raven Press Books, Ltd., New York, 1984, pp. 7-13, 54-60; Spilker B., *Guide to Clinical Trials*, Raven Press, Ltd., New York, 1991, pp. 93-101; Craig C., and R. Stitzel, eds., *Modern Pharmacology*, 2d ed., Little, Brown and Co., Boston, 1986, pp. 127-33; T. Speight, ed., *Avery's Drug Treatment: Principles and Practice of Clinical Pharmacology and Therapeutics*, 3d ed., Williams and Wilkins, Baltimore, 1987, pp. 50-56; R. Tallarida, R. Raffa and P. McGonigle, *Principles in General Pharmacology*, Springer-Verlag, New York, 1988, pp. 18-20. Generally, inclusive final concentrations in the range of about 0.1 mg/kg to 1000 mg/kg, more specifically between about 1.0 mg/kg and 500 mg/kg, and preferably from about 10 mg/kg and 100 mg/kg, are administered per day to an adult in any pharmaceutically-acceptable carrier.

Dose and Administration

The compositions, as described herein, are administered in effective amounts. As discussed above, the effective amount depends upon the mode of administration, the particular condition being treated, and the desired outcome. It also depends upon the stage of the condition, the age and physical condition of the subject, the nature of concurrent therapy, if any, and like factors well known to the medical practitioner. For therapeutic applications, it is that amount sufficient to achieve a medically desirable result.

In one embodiment, the dose of the composition of the present disclosure is less than 1 mg/kg, between about 1 mg/kg and about 200 mg/kg, about 200 mg/kg and about 400 mg/kg, about 400 mg/kg and about 600 mg/kg, about 600 mg/kg and about 800 mg/kg, about 800 mg/kg and about 1000 mg/kg body weight, or more than 1000 mg/kg body weight per day, inclusive of all values and ranges therebetween, including endpoints. In one embodiment, the dose is from about 10 mg/kg to about 200 mg/kg per day. In one embodiment, the dose is from about 200 mg/kg to about 400 mg/kg per day. In one embodiment, the dose does not exceed about 1000 mg/kg per day.

In one embodiment, the dose of fusaricidin is about 0.01 mg/kg to about 100 mg/kg, from about 0.02 mg/kg to about 50 mg/kg, from about 0.05 mg/kg to about 30 mg/kg, from about 0.1 mg/kg to about 20 mg/kg, from about 0.2 mg/kg to about 10 mg/kg, from about 0.2 mg/kg to about 5 mg/kg, or from about 0.3 mg/kg to about 1 mg/kg. In some embodiments, the dosage of the fusaricidin is at least 0.01 mg/kg, at least 0.02 mg/kg, at least 0.05 mg/kg, at least 0.1 mg/kg, at least 0.2 mg/kg, at least 0.3 mg/kg, at least 0.4 mg/kg, at least 0.5 mg/kg, at least 0.6 mg/kg, at least 0.7 mg/kg, at least 0.8 mg/kg, at least 0.9 mg/kg, at least 1 mg/kg, at least 2 mg/kg, at least 5 mg/kg, at least 10 mg/kg, at least 20 mg/kg, at least 30 mg/kg, at least 40 mg/kg, at least 50 mg/kg, at least 60 mg/kg, at least 70 mg/kg, at least 80 mg/kg, at least 90 mg/kg, or at least 100 mg/kg.

In one aspect of the invention, the composition or fusaricidin of this disclosure is administered every 1 hour to every 24 hours; for example, every 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. In one embodiment, the composition or fusaricidin is administered every one day, two days, three days, four days, five days, six days, seven days, eight days, nine days, or ten days.

In one aspect of the invention, doses of the pharmaceutical composition are administered for a period of time sufficient to have an anti-pathogen effect (e.g., to attenuate the risk of pathogen or infectious disease). In one embodiment, the period of time is between about one day and about ten days. For example, the period of time may be one day, two days, three days, four days, five days, six days, seven days, eight days, nine days, or ten days.

A variety of administration routes are available. The pharmaceutical composition of the invention, generally speaking, may be practiced using any mode of administration that is medically acceptable, meaning any mode that produces effective levels of the active ingredients without causing clinically unacceptable adverse effects.

Routes of administration that are appropriate in the practice of the present invention include, but are not limited to, oral, rectal, topical, nasal, intradermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule.

Compositions suitable for oral administration may be presented as discrete units, such as capsules, tablets, or lozenges, each containing a predetermined amount of the active agent(s). The compositions can take any form that is appropriate for the practice of the present disclosure, which includes but is not limited to solutions, suspensions (e.g., elixirs or syrups), emulsion, tablets, capsules, powders, suppositories, implants, sustained-release formulations, and the like, depending on the route of administration chosen.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions, or suspensions, including saline and buffered media. Parenteral vehicles include sodium chloride solution, Ringer's dextrose, dextrose and sodium chloride, lactated Ringer's, or 25 fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, inert gases, and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

Other delivery systems can include time-release, delayed release or sustained release delivery systems. Such systems can avoid repeated administrations of the pharmaceutical composition of this invention, increasing convenience to the subject and the physician. Many types of release delivery systems are available and known to those of ordinary skill in the art. They include polymer base systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters, and fatty acids or neutral fats such as mono-, di-, and tri-glycerides; hydrogel release systems; silastic systems; peptide-based systems; wax coatings; compressed tablets using conventional binders and excipients; partially fused implants; and the like.

In one embodiment, the composition or the fusaricidin is administered in a time-release, delayed release, or sustained release delivery system. In one embodiment, the time-release, delayed release, or sustained release delivery system comprising the pharmaceutical composition of the invention is inserted directly into the tumor.

When administered, the composition of the invention are applied in pharmaceutically-acceptable amounts and in pharmaceutically-acceptable compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically acceptable salts can be prepared as alkaline metal or alkaline earth salts, such as sodium, potassium, or calcium salts.

In one aspect of this invention is provided a method for treating and/or preventing an infectious disease in a subject, comprising administering to the subject an effective amount of the composition comprising a fusaricidin.

Non-limiting examples of infectious diseases that can be treated or targeted by the compositions and methods described herein include, but are not limited to, *Acinetobacter* infections, Actinomycosis, African sleeping sickness, AIDS (Acquired immunodeficiency syndrome), Amebiasis, Anaplasmosis, Angiostrongyliasis, Anisakiasis, Anthrax, *Arcanobacterium haemolyticum* infection, Argentine hemorrhagic fever, Ascariasis, Aspergillosis, Astrovirus infection, Babesiosis, *Bacillus cereus* infection, Bacterial pneumonia, Bacterial vaginosis, *Bacteroides* infection, Balantidiasis, Bartonellosis, *Baylisascaris* infection, BK virus infection, Black piedra, Blastocystosis, Blastomycosis, Bolivian hemorrhagic fever, Botulism (and Infant botulism), Brazilian hemorrhagic fever, Brucellosis, Bubonic plague, *Burkholderia* infection, Buruli ulcer, Calicivirus infection (Norovirus and Sapovirus), Campylobacteriosis, Candidiasis (Moniliasis; Thrush), Capillariasis, Carrion's disease, Cat-scratch disease, Cellulitis, Chagas Disease (American trypanosomiasis), Chancroid, Chickenpox, Chikungunya, *Chlamydia, Chlamydophila pneumoniae* infection (Taiwan acute respiratory agent or TWAR), Cholera, Chromoblastomycosis, Chytridiomycosis, Clonorchiasis, *Clostridium difficile* colitis, Coccidioidomycosis, Colorado tick fever (CTF), Common cold (Acute viral rhinopharyngitis; Acute coryza), Creutzfeldt-Jakob disease (CJD), Crimean-Congo hemorrhagic fever (CCHF), Cryptococcosis, Cryptosporidiosis, Cutaneous larva migrans (CLM), Cyclosporiasis, Cysticercosis, Cytomegalovirus infection, Dengue fever, Desmodesmus infection, Dientamoebiasis, Diphtheria, Diphyllobothriasis, Dracunculiasis, Ebola hemorrhagic fever, Echinococcosis, Ehrlichiosis, Enterobiasis (Pinworm infection), *Enterococcus* infection, Enterovirus infection, Epidemic typhus, Erythema infectiosum (Fifth disease), Exanthem subitum (Sixth disease), Fascioliasis, Fasciolopsiasis, Fatal familial insomnia (FFI), Filariasis, Food poisoning by *Clostridium perfringens*, Free-living amebic infection, *Fusobacterium* infection, Gas gangrene (Clostridial myonecrosis), Geotrichosis, Gerstmann-Straussler-Scheinker syndrome (GSS), Giardiasis, Glanders, Gnathostomiasis, Gonorrhea, Granuloma inguinale (Donovanosis), Group A streptococcal infection, Group B streptococcal infection, *Haemophilus influenzae* infection, Hand, foot and mouth disease (HFMD), Hantavirus Pulmonary Syndrome (HPS), Heartland virus disease, *Helicobacter pylori* infection, Hemolytic-uremic syndrome (HUS), Hemorrhagic fever with renal syndrome (HFRS), Hepatitis A, Hepatitis B, Hepatitis C, Hepatitis D, Hepatitis E, Herpes simplex, Histoplasmosis, Hookworm infection, Human bocavirus infection, Human ehrlichiosis ewingii, Human granulocytic anaplasmosis (HGA), Human metapneumovirus infection, human monocytic ehrlichiosis, Human papillomavirus (HPV) infection, Human parainfluenza virus infection, Hymenolepiasis, Epstein-Barr virus infectious mononucleosis (Mono), Influenza (flu), Isosporiasis, Kawasaki disease, Keratitis, Kingella kingae infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever (MHF), Measles, Middle East respiratory syndrome (MERS), Melioidosis (Whitmore's disease), Meningitis, Meningococcal disease, Metagonimiasis, Microsporidiosis, Molluscum contagiosum (MC), Monkeypox, Mumps, Murine typhus (Endemic typhus), *Mycoplasma* pneumonia, Mycetoma (disambiguation), Myiasis, Neonatal conjunctivitis (Ophthalmia neonatorum), Variant Creutzfeldt-Jakob disease (vCJD, nvCJD), Nocardiosis, Onchocerciasis (River blindness), Opisthorchiasis, Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Plague, Pneumococcal infection, *Pneumocystis* pneumonia (PCP), Pneumonia, Poliomyelitis, *Prevotella* infection, Primary amoebic meningoencephalitis (PAM), Progressive multifocal leukoencephalopathy, Psittacosis, Q fever, Rabies, Relapsing fever, Respiratory syncytial virus infection, Rhinosporidiosis, Rhinovirus infection, Rickettsial infection, Rickettsialpox, Rift Valley fever (RVF), Rocky Mountain spotted fever (RMSF), Rotavirus infection, Rubella, *Salmonellosis*, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Subacute sclerosing panencephalitis, Syphilis, Taeniasis, Tetanus (Lockjaw), *Tinea* barbae (Barber's itch), *Tinea capitis* (Ringworm of the Scalp), *Tinea corporis* (Ringworm of the Body), *Tinea cruris* (Jock itch), *Tinea manuum* (Ringworm of the Hand), *Tinea nigra, Tinea pedis* (Athlete's foot), *Tinea unguium* (Onychomycosis), *Tinea versicolor* (*Pityriasis versicolor*), Toxocariasis (Ocular Larva Migrans (OLM)), Toxocariasis (Visceral Larva Migrans (VLM)), Trachoma, Toxoplasmosis, Trichinosis, Trichomoniasis, Trichuriasis (Whipworm infection), Tuberculosis, Tularemia, Typhoid fever, Typhus fever, *Ureaplasma urealyticum* infection, Valley fever, Venezuelan equine encephalitis, Venezuelan hemorrhagic fever, *Vibrio vulnificus* infection, *Vibrio parahaemolyticus* enteritis, Viral pneumonia, West Nile Fever, White *piedra* (*Tinea* blanca), *Yersinia pseudotuberculosis* infection, Yersiniosis, Yellow fever, and Zygomycosis.

Kit of Parts

In one aspect, this invention relates to a kit of parts for treatment of an infectious disease or a pathogen in a subject, the kit comprising a fusaricidin. The fusaricidin of the disclosure has a same or similar structure with a metabolite produced by a bacterium of *Paenibacillus* or *Bacillus*. The bacteria comprise, consist essentially of, or yet consist of MS1479, MS2379, MS2414, MS2820, MS0633, MS2335, MS2652, MS2658, MS2681, MS2697, or MS2712.

In another embodiment, the fusaricidin is a cyclic fusaricidin or an open-chain fusaricidin. The identified cyclic fusaricidins have a ring structure with six amino acid residues at different positions, wherein the ring structure has a 15-guanidino-3-hydroxypentadecanoyl (GHPD) side chain or 17-guanidino-3-(R)-hydroxyheptadecanoyl (GHHD) side chain. In one embodiment, the cyclic fusaricidin is a compound of Formula I, wherein $X_1$ is Thr or Ser; $X_2$ is Val or Ile; $X_3$ is selected from a group consisting of Val, Ile, Tyr, and Phe; $X_4$ is Thr or Ser; $X_5$ is Asn or Gln; $X_6$ is Ala; wherein $R_1$ is a 15-guanidino-3-hydroxypentadecanoyl (GHPD) side chain or 17-guanidino-3-(R)-hydroxyheptadecanoyl (GHHD) side chain.

In another embodiment, the open-chain fusaricidin is a compound of Formula II, wherein $X_7$ is Thr or Ser; $X_8$ is Val or Ile; $X_9$ is selected from a group consisting of Val, Ile, Tyr, and Phe; $X_{10}$ is Thr or Ser; $X_{11}$ is Asn or Gln; $X_{12}$ is selected from a group consisting of Ala, GABA, and Gly; wherein $R_1$ is a GHPD side chain. For example, No. 29 fusaricidin has a formula of $C_{40}H_{74}N_{10}O_{12}$ and a GHPD side chain. On the amino acid chain of fusaricidin No. 29, Ser is at the position 7, Val at position 8, Val at position 9, Thr at position 10, Asn at position 11, and Ala at position 12.

In some embodiments, the kit further comprises, alternatively consists essentially of, or yet consists of an antibiotic for combination or synergistic therapy.

In one embodiment, the kit further comprises instructions for treating the infectious disease. In one embodiment, the kit of parts comprises instructions for dosing and/or administration of the composition or the fusaricidin of this disclosure.

WORKING EXAMPLES

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends, and advantages inherent herein. The present examples, along with the methods described herein, are presently representative of embodiments and are exemplary and are not intended as limitations on the scope of the disclosure. Changes therein and other uses which are encompassed within the disclosure as defined by the scope of the claims will occur to those skilled in the art.

Example 1 In Vitro Inhibition of Pathogens

Fifty organic extracts were prepared from 25 whole broth of four microbial strains (MS1479, MS2379, MS2820, and MS2414), which were fermented in different media for the antimicrobial testing. Note each whole broth culture generated one n-butanol extract from cultural supernatant and one methanol extract from cell pellets.

Figure 2:
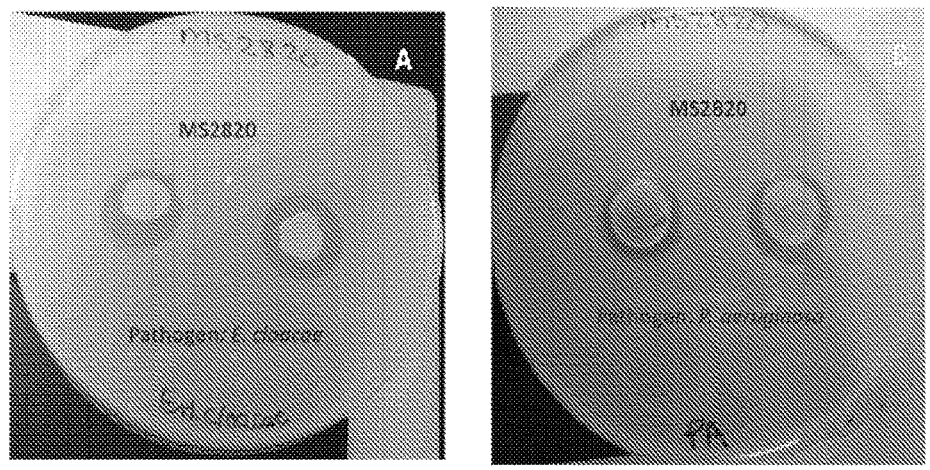
FIG. 2 depicts the in vitro inhibition of ESKAPE pathogens by Paenibacilli strains (MS2820).

The antimicrobial activities of the 50 organic extracts were studied against three fungal pathogens—*Candida albicans, Aspergillus fumigatus*, and *Cryptococcus neoformans*—and five bacterial strains-Methicillin-resistant *Staphylococcus aureus* (MIRSA), *Escherichia coli, Pseudomonas aeruginosa, Klebsiella pneumoniae*, and Vancomycin-resistant *Enterococcus faecium* (VRE) (FIG. 2). The test concentrations for all extracts were in the range of 8-200 μg/mL (Table 3).

TABLE 3

| Sample_Name | C. albicans IC50 | A. fumigatus IC50 | C. neoformans IC50 | MRS IC50 | E. coli IC50 | P. aeruginosa IC50 | K pneumoniae IC50 | VRE IC50 | Test Conc. |
|---|---|---|---|---|---|---|---|---|---|
| Fluconazole | <0.1 | >100 | 2.20 | >100 | >100 | >100 | >100 | >100 | 100-4 μg/mL |
| Amphotericin B (New Lot) | <0.1 | 1.407 | 0.24 | >100 | >100 | >100 | >100 | >100 | 100-4 μg/mL |
| Ciprofloxacin (New Lot) | >10 | >10 | >10 | >10 | <0.01 | 0.81 | >10 | >10 | 10-0.4 μg/mL |
| Vancomycin | >100 | >100 | >100 | 0.17 | 67.41 | >100 | >100 | >100 | 100-4 μg/mL |
| Methicillin | >100 | >100 | >100 | 19.00 | >100 | 95.42 | >100 | >100 | 100-4 μg/mL |
| Cefotaxime | >100 | >100 | >100 | 14.80 | 80.20 | 11.83 | >100 | >100 | 100-4 μg/mL |
| Meropenem | >100 | >100 | >100 | 2.75 | 11.50 | >100 | 18.15 | >100 | 100-4 μg/mL |
| MS1479-BS3-M2-Supernatant n-BuOH Extract | >200 | >200 | 19.77 | 97.46 | 54.56 | 110.76 | 95.27 | >200 | 200-8 μg/mL |
| MS1479-GB6-M3-Supernatant n-BuOH Extract | >200 | >200 | 71.76 | 121.59 | >200 | >200 | >200 | >200 | 200-8 μg/mL |
| MS2379-BS3-M2-Supernatant n-BuOH Extract | >200 | >200 | 73.19 | 92.99 | >200 | >200 | >200 | >200 | 200-8 μg/mL |
| MS2379-GB6-M3-Supernatant n-BuOH Extract | 130.44 | >200 | 40.22 | <8 | >200 | >200 | >200 | <8 | 200-8 μg/mL |
| MS2414-BS3-M2-Supernatant n-BuOH Extract | >200 | >200 | 10.09 | 83.64 | 91.57 | 76.88 | 100.18 | >200 | 200-8 μg/mL |
| MS2414-GB6-M3-Supernatant n-BuOH Extract | >200 | >200 | 25.75 | 73.01 | 175.74 | >200 | >200 | >200 | 200-8 μg/mL |
| MS2820-BS3-M2-Supernatant n-BuOH Extract | 163.61 | >200 | 15.71 | 15.74 | 49.20 | >200 | >200 | 96.24 | 200-8 μg/mL |
| MS2820-GB6-M3-Supernatant n-BuOH Extract | >200 | >200 | 15.21 | 95.21 | 67.27 | >200 | >200 | 82.13 | 200-8 μg/mL |
| MS1479-GB6-M8-Supernatant n-BuOH Extract | 81.45 | >200 | 18.01 | 16.93 | 55.51 | 149.68 | >200 | 113.23 | 200-8 μg/mL |
| MS2379-GB6-M8-Supernatant n-BuOH Extract | 78.95 | >200 | 15.61 | 20.36 | 177.68 | >200 | >200 | 158.09 | 200-8 μg/mL |
| MS2414-GB6-M8-Supernatant n-BuOH Extract | 136.76 | >200 | 14.90 | 21.84 | 34.41 | 43.34 | 30.90 | 127.11 | 200-8 μg/mL |
| MS2820-GB6-M8-Supernatant n-BuOH Extract | 42.65 | >200 | <8 | 20.58 | 45.63 | >200 | >200 | 15.77 | 200-8 μg/mL |
| MS2414-TSB-Supernatant n-BuOH Extract | >200 | >200 | >200 | >200 | >200 | >200 | >200 | >200 | 200-8 μg/mL |
| MS2414-GB6-M3-Supernatant n-BuOH Extract | >200 | >200 | 13.98 | 90.71 | 176.53 | >200 | >200 | >200 | 200-8 μg/mL |

TABLE 3-continued

The antimicrobial activities of 50 microbial extracts (IC50, μg/mL)

| Sample_Name | C. albicans IC50 | A. fumigatus IC50 | C. neoformans IC50 | MRS IC50 | E. coli IC50 | P. aeruginosa IC50 | K pneumoniae IC50 | VRE IC50 | Test Conc. |
|---|---|---|---|---|---|---|---|---|---|
| MS2414-GB6-M8-Supernatant n-BuOH Extract | >200 | >200 | 16.40 | 72.70 | 61.07 | 83.18 | 58.91 | >200 | 200-8 μg/mL |
| MS2414-GB6-M10-Supernatant n-BuOH Extract | 167.03 | >200 | 19.29 | 21.87 | 55.14 | 105.73 | 61.93 | 185.65 | 200-8 μg/mL |
| MS2414-BS3-M2-Supernatant n-BuOH Extract | >200 | >200 | 16.89 | 159.99 | 164.63 | 94.52 | 61.76 | 198.71 | 200-8 μg/mL |
| MS2414-BS3-M9-Supernatant n-BuOH Extract | 195.47 | >200 | 15.11 | 90.32 | 56.46 | 81.10 | 156.84 | >200 | 200-8 μg/mL |
| MS2414-BS3-M10-Supernatant n-BuOH Extract | 167.21 | >200 | 15.15 | 18.62 | >200 | >200 | >200 | 171.12 | 200-8 μg/mL |
| MS2414-GB6-M3-Supernatant n-BuOH Extract | >200 | >200 | 15.94 | 126.27 | >200 | >200 | >200 | 163.72 | 200-8 μg/mL |
| MS2414-GB6-M3 (48 h)Supernatant n-BuOH Extract | >200 | >200 | 14.68 | 162.68 | 147.57 | >200 | >200 | >200 | 200-8 μg/mL |
| MS2414-GB6-M3 (71 h)-Supernatant n-BuOH Extract | >200 | >200 | 13.74 | 48.74 | 121.90 | >200 | 164.42 | >200 | 200-8 μg/mL |
| MS2414-BS3-M2 (24 h)-Supernatant n-BuOH Extract | >200 | >200 | 14.76 | 16.60 | 140.79 | >200 | 170.59 | 177.34 | 200-8 μg/mL |
| MS2414-BS3-M2 (48 h)-Supernatant n-BuOH Extract | >200 | >200 | 15.34 | 22.02 | >200 | >200 | >200 | 181.85 | 200-8 μg/mL |
| MS2414-BS3-M2 (71 h)-Supernatant n-BuOH Extract | >200 | >200 | 15.77 | 30.15 | 148.0 | >200 | >200 | 185.85 | 200-8 μg/mL |
| MS1479-BS3-M2-Cell Pellets MeOH Extract | 190.81 | >200 | <8 | 18.08 | 156.7 | >200 | >200 | 15.80 | 200-8 μg/mL |
| MS1479-GB6-M3-Cell Pellets MeOH Extract | 43.36 | >200 | <8 | 21.19 | 186.6 | >200 | >200 | 15.18 | 200-8 μg/mL |
| MS2379-BS3-M2-Cell Pellets MeOH Extract | >200 | >200 | <8 | 18.14 | >200 | >200 | >200 | >200 | 200-8 μg/mL |
| MS2379-GB6-M3-Cell Pellets MeOH Extract | 24.14 | >200 | <8 | <8 | 50.45 | >200 | >200 | 8.48 | 200-8 μg/mL |
| MS2414-BS3-M2-Cell Pellets MeOH Extract | >200 | >200 | 8.21 | 31.40 | >200 | >200 | >200 | 98.08 | 200-8 μg/mL |
| MS2414-GB6-M3-Cell Pellets MeOH Extract | 76.48 | >200 | <8 | 10.85 | >200 | >200 | >200 | 31.91 | 200-8 μg/mL |
| MS2820-BS3-M2-Cell Pellets MeOH Extract | 200 | >200 | 15.53 | 29.44 | 68.73 | >200 | >200 | 80.61 | 200-8 μg/mL |
| MS2820-GB6-M3-Cell Pellets MeOH Extract | 158.74 | >200 | <8 | 30.31 | >200 | >200 | >200 | 23.09 | 200-8 μg/mL |
| MS1479-GB6-M8-Cell Pellets MeOH Extract | 102.40 | >200 | 22.61 | 43.38 | >200 | >200 | >200 | 76.06 | 200-8 μg/mL |
| MS2379-GB6-M8-Cell Pellets MeOH Extract | 19.07 | >200 | <8 | 10.02 | 147.43 | >200 | >200 | 19.13 | 200-8 μg/mL |
| MS2414-GB6-M8-Cell Pellets MeOH Extract | 37.79 | >200 | <8 | <8 | >200 | >200 | >200 | 20.16 | 200-8 μg/mL |
| MS2820-GB6-M8-Cell Pellets MeOH Extract | 42.59 | >200 | <8 | <8 | 200 | >200 | >200 | 21.28 | 200-8 μg/mL |

TABLE 3-continued

The antimicrobial activities of 50 microbial extracts (IC50, μg/mL)

| Sample_Name | C. albicans IC50 | A. fumigatus IC50 | C. neoformans IC50 | MRS IC50 | E. coli IC50 | P. aeruginosa IC50 | K pneumoniae IC50 | VRE IC50 | Test Conc. |
|---|---|---|---|---|---|---|---|---|---|
| MS2414-TSB-Cell Pellets MeOH Extract | >200 | >200 | >200 | >200 | >200 | >200 | >200 | 190.32 | 200-8 μg/mL |
| MS2414-GB6-M3-Cell Pellets MeOH Extract | >200 | >200 | 18.58 | 21.51 | >200 | >200 | >200 | 169.00 | 200-8 μg/mL |
| MS2414-GB6-M8-Cell Pellets MeOH Extract | 53.23 | >200 | <8 | <8 | >200 | >200 | >200 | 32.95 | 200-8 μg/mL |
| MS2414-GB6-M10-Cell Pellets MeOH Extract | 41.39 | >200 | <8 | <8 | >200 | >200 | >200 | 32.43 | 200-8 μg/mL |
| MS2414-BS3-M2-Cell Pellets MeOH Extract | 200 | >200 | 15.34 | 14.67 | >200 | >200 | >200 | 39.79 | 200-8 μg/mL |
| MS2414-BS3-M9-Cell Pellets MeOH Extract | 122.17 | >200 | 13.98 | 18.10 | >200 | >200 | >200 | 163.75 | 200-8 μg/mL |
| MS2414-BS3-M10-Cell Pellets MeOH Extract | >200 | >200 | 18.76 | 70.32 | >200 | >200 | >200 | >200 | 200-8 μg/mL |
| MS2414-GB6-M3-Cell Pellets MeOH Extract | >200 | >200 | 17.43 | 143.63 | >200 | >200 | >200 | 164.09 | 200-8 μg/mL |
| MS2414-GB6-M3 (48 h)-Cell Pellets MeOH Extract | 196.68 | >200 | 18.93 | 17.59 | >200 | >200 | >200 | 164.47 | 200-8 μg/mL |
| MS2414-GB6-M3 (71 h)-Cell Pellets MeOH Extract | >200 | >200 | <8 | 17.20 | >200 | >200 | >200 | 181.16 | 200-8 μg/mL |
| MS2414-BS3-M2 (24 h)-Cell Pellets MeOH Extract | >200 | >200 | 8.14 | 14.68 | >200 | >200 | >200 | 173.82 | 200-8 μg/mL |
| MS2414-BS3-M2 (48 h)-Cell Pellets MeOH Extract | >200 | >200 | <8 | 16.46 | >200 | >200 | >200 | 40.41 | 200-8 μg/mL |
| MS2414-BS3-M2 (71 h)-Cell Pellets MeOH Extract | 195.83 | >200 | <8 | 8.52 | >200 | >200 | >200 | 31.47 | 200-8 μg/mL |

The results indicated that all the 50 extracts except the two from MS2414-TSB were active against C. neoformans and MRSA, while many extracts showed varying degrees of activities against C. albicans, E. coli, P. aeruginosa, K. pneumoniae, and VRE. Generally, the n-butanol extract from cultural supernatant and the methanol extract from cell pellets for each strain at specific fermentation conditions showed similar activity profiles.

In addition to the findings that some extracts showed potent activity against C. neoformans and MRSA (IC50<8 μg/mL), it was noted that a few extracts showed excellent activities against VRE. For example, MS2379-GB6-M3 n-butanol extract and methanol extract exhibited IC50 values of <8 and 8.44 μg/mL, respectively, against VRE.

Without being bound by a theory, the extracts' activities against VRE (and C. albicans) did not always correlate with the ratio of fusaricidin A/total fusaricidins. For example, MS2379-GB6-M3 produced almost the least amount of fusaricidin A (101.07 mg/L) among the 25 microbial samples analyzed (see Sample #4 in Table 4). Without being bound by a theory, in addition to fusaricidin A, other fusaricidins and/or possibly novel compounds may be responsible for the potent anti-VRE activity observed for the extracts. The genome sequences show that MS2379 may be a new Paenibacillus species because it is less affiliated with P. polymyxa as are the other three bacterial strains.

The 50 organic extracts were analyzed by LC-MS to measure the production of fusaricidins. Fusaricidin A, an antifungal compound produced in the MS2414 strain, was used as a baseline to generate a quantification curve based on the concentrations against the peak areas of positive ESIMS extracted ion chromatograms. The contents of fusaricidin A in these samples are summarized in Table 4, which shows that the n-butanol extracts generally contain less fusaricidin A compared to the methanol extracts. For example, Sample #1 produced only 5.15 mg/L fusaricidin A from n-butanol extracts, but 259.15 mg/L from the methanol extracts. Without being bound by a theory, the results may indicate that fusaricidin A (and other analogs) mainly stayed in the cells. The filtrate samples (which would be similar to the supernatants generated by centrifugation) also contained negligible amounts of fusaricidin A. The contents of fusaricidin A in the 25 whole broth cultural samples are in the range 3.6-341.39 mg/L, with MS2820-BS3-M2 (#7), MS2414-BS3-M10 (#23), and MS2414-GB-6-M3 (#18) on the top 3 list, all of which produced fusaricidin A greater than 300 mg/L.

TABLE 4

Quantification of Fusaricidin A in Microbial Strains

| Sample | Sample Description | Extract (mg) | | Conc. of Fusaricidin A (mg/L) |
|---|---|---|---|---|
| #1 | MS1479-BS3-M2-Supernatant n-BuOH Extract | 11.4 | 5.15 | 264.62 |
| | MS1479-BS3-M2-Cell Pellets MeOH Extract | 36.8 | 259.47 | |
| #2 | MS1479-GB6-M3-Supernatant n-BuOH Extract | 9.4 | 6.07 | 246.19 |
| | MS1479-GB6-M3-Cell Pellets MeOH Extract | 17.7 | 240.12 | |
| #3 | MS2379-BS3-M2-Supernatant n-BuOH Extract | 10.1 | 1.79 | 171.55 |
| | MS2379-BS3-M2-Cell Pellets MeOH Extract | 25.6 | 169.76 | |
| #4 | MS2379-GB6-M3-Supernatant n-BuOH Extract | 7.6 | 2.23 | 101.07 |
| | MS2379-GB6-M3-Cell Pellets MeOH Extract | 18.2 | 98.84 | |
| #5 | MS2414-BS3-M2-Supernatant n-BuOH Extract | 9.8 | 3.46 | 203.31 |
| | MS2414-BS3-M2-Cell Pellets MeOH Extract | 26.6 | 199.85 | |
| #6 | MS2414-GB6-M3-Supernatant n-BuOH Extract | 7.2 | 3.50 | 216.51 |
| | MS2414-GB6-M3-Cell Pellets MeOH Extract | 15.8 | 213.01 | |
| #7 | MS2820-BS3-M2-Supernatant n-BuOH Extract | 10.3 | 16.0 | 341.39 |
| | MS2820-BS3-M2-Cell Pellets MeOH Extract | 46.2 | 325.39 | |
| #8 | MS2820-GB6-M3-Supernatant n-BuOH Extract | 7.2 | 4.60 | 234.68 |
| | MS2820-GB6-M3-Cell Pellets MeOH Extract | 23.8 | 230.38 | |
| #9 | MS1479-BS3-M2-Filtrate | | | ~0? |
| #10 | MS2379-BS3-M2-Filtrate | | | ~2.00? |
| #11 | MS2414-BS3-M2-Filtrate | | | ~0? |
| #12 | MS2820-BS3-M2-Filtrate | | | ~3.92? |
| #13 | MS1479-GB6-M8-Supernatant n-BuOH Extract | 6.8 | 17.79 | 193.85 |
| | MS1479-GB6-M8-Cell Pellets MeOH Extract | 27.7 | 176.06 | |
| #14 | MS2379-GB6-M8-Supernatant n-BuOH Extract | 5.8 | 9.96 | 184.21 |
| | MS2379-GB6-M8-Cell Pellets MeOH Extract | 21 | 174.25 | |
| #15 | MS2414-GB6-M8-Supernatant n-BuOH Extract | 7.4 | 8.33 | 163.98 |
| | MS2414-GB6-M8-Cell Pellets MeOH Extract | 13.1 | 155.65 | |
| #16 | MS2820-GB6-M8-Supernatant n-BuOH Extract | 9.7 | 45.07 | 115.59 |
| | MS2820-GB6-M8-Cell Pellets MeOH Extract | 24.9 | 70.52 | |
| #17 | MS2414-TSB-Supernatant n-BuOH Extract | 17.6 | 00 | 3.60 |
| | MS2414-TSB-Cell Pellets MeOH Extract | 4.7 | 3.60 | |
| #18 | MS2414-GB6-M3-Supernatant n-BuOH Extract | 7.5 | 5.66 | 314.61 |
| | MS2414-GB6-M3-Cell Pellets MeOH Extract | 41.4 | 308.95 | |
| #19 | MS2414-GB6-M8-Supernatant n-BuOH Extract | 7.8 | 6.92 | 139.52 |
| | MS2414-GB6-M8-Cell Pellets MeOH Extract | 11.4 | 132.60 | |
| #20 | MS2414-GB6-M10-Supernatant n-BuOH Extract | 7.4 | 13.28 | 104.40 |
| | MS2414-GB6-M10-Cell Pellets MeOH Extract | 12.7 | 91.12 | |
| #21 | MS2414-BS3-M2-Supernatant n-BuOH Extract | 8.2 | 11.07 | 293.11 |
| | MS2414-BS3-M2-Cell Pellets MeOH Extract | 45.5 | 282.06 | |
| #22 | MS2414-BS3-M9-Supernatant n-BuOH Extract | 5.3 | 13.57 | 138.66 |
| | MS2414-BS3-M9-Cell Pellets MeOH Extract | 32.3 | 125.09 | |
| #23 | MS2414-BS3-M10-Supernatant n-BuOH Extract | 4.9 | 21.77 | 339.67 |
| | MS2414-BS3-M10-Cell Pellets MeOH Extract | 44 | 317.90 | |
| #24 | MS2414-GB6-M3-Supernatant n-BuOH Extract | 9.5 | 12.92 | 103.63 |
| | MS2414-GB6-M3-Cell Pellets MeOH Extract | 20.1 | 90.71 | |
| #25 | MS2414-GB6-M3 (48 h)-Supernatant n-BuOH Extract | 7.3 | 3.74 | 231.18 |
| | MS2414-GB6-M3 (48 h)-Cell Pellets MeOH Extract | 22.8 | 227.44 | |
| #26 | MS2414-GB6-M3 (71 h)-Supernatant n-BuOH Extract | 6 | 3.44 | 227.63 |
| | MS2414-GB6-M3 (71 h)-Cell Pellets MeOH Extract | 17.1 | 224.19 | |
| #27 | MS2414-BS3-M2 (24 h)-Supernatant n-BuOH Extract | 9.2 | 6.44 | 70.91 |
| | MS2414-BS3-M2 (24 h)-Cell Pellets MeOH Extract | 40.3 | 64.47 | |
| #28 | MS2414-BS3-M2 (48 h)-Supernatant n-BuOH Extract | 6.8 | 13.28 | 282.59 |
| | MS2414-BS3-M2 (48 h)-Cell Pellets MeOH Extract | 39.8 | 269.31 | |
| #29 | MS2414-BS3-M2 (71 h)-Supernatant n-BuOH Extract | 6.2 | 15.19 | 170.01 |
| | MS2414-BS3-M2 (71 h)-Cell Pellets MeOH Extract | 21.9 | 154.82 | |

TABLE 5

Summary of potent antibiosis against pathogens by *Paenibacillus* strains (IC50, µg/mL)

| Sample_Name | C. albicans IC50 | A. fumigatus IC50 | C. neoformans IC50 | MRS IC50 | VRE IC50 |
|---|---|---|---|---|---|
| Fluconazole | <0.1 | >100 | 2.20 | >100 | >100 |
| Amphotericin B | <0.1 | 1.407 | 0.24 | >100 | >100 |
| Ciprofloxacin | >10 | >10 | >10 | >10 | >10 |
| Vancomycin | >100 | >100 | >100 | 0.17 | >100 |
| Methicillin | >100 | >100 | >100 | 19.00 | >100 |
| Cefotaxime | >100 | >100 | >100 | 14.80 | >100 |
| Meropenem | >100 | >100 | >100 | 2.75 | >100 |

TABLE 5-continued

Summary of potent antibiosis against pathogens by *Paenibacillus* strains (IC50, µg/mL)

| Sample_Name | *C. albicans* IC50 | *A. fumigatus* IC50 | *C. neoformans* IC50 | MRS IC50 | VRE IC50 |
|---|---|---|---|---|---|
| MS2379-GB6-M3-Supernatant | 130.44 | >200 | 40.22 | <8 | <8 |
| MS2820-GB6-M8-Supernatant | 42.65 | >200 | <8 | 20.58 | 15.77 |
| MS1479-BS3-M2-Cell Pellets | 190.81 | >200 | <8 | 18.08 | 15.80 |
| MS1479-GB6-M3-Cell Pellets | 43.36 | >200 | <8 | 21.19 | 15.18 |
| MS2379-GB6-M3-Cell Pellets | 24.14 | >200 | <8 | <8 | 8.48 |
| MS2379-GB6-M8-Cell Pellets | 19.07 | >200 | <8 | 10.02 | 19.13 |
| MS2414-GB6-M8-Cell Pellets | 37.79 | >200 | <8 | <8 | 20.16 |
| MS2820-GB6-M8-Cell Pellets | 42.59 | >200 | <8 | <8 | 21.28 |
| MS2414-BS3-M2 (48 h)-Cell Pellets | >200 | >200 | <8 | 16.46 | 40.41 |
| MS2414-BS3-M2 (71 h)-Cell Pellets | 195.83 | >200 | <8 | 8.52 | 31.47 |

Example 2 ESKAPE Pathogen Screening

The 4 *Paenibacillus* strains (MS1479, MS2379, MS2414 and MS2820) were tested along with other spore-forming bacteria for antibiosis against ESKAPE pathogens (*Enterococcus faecium* ATCC 70021, *Staphylococcus aureus* Xen 29 PerkinElmer, *Klebsiella pneumoniae* 3363 Walter Reed, *Acinetobacter baumannii* 3806 Walter Reed, *Pseudomonas aeruginosa* ATCC 27853, and *Enterobacter cloacae* ATCC BAA-1143 strain 55M).

In the experiment, water agar plates were prepared with two punched holes per plate. Each hole was filled with Tryptic Soy Agar (TSA), which was allowed to dry. The plates were stored at 4° C. On Day 1, the bacteria were cultured in 2.0 ml of TSB and inoculated with isolated colony from plate. The cultures were incubated at 30° C. with shaking at 200 rpm for 24 hours.

On Day 2, the broth cultures were checked for growth. If the culture appeared turbid, 10 microliters of the cultures were added onto each of the TSA circles on the water agar plates. The cultures were allowed to dry and were incubated for 48 hours at 30° C.

On Day 3, the plates were checked for the bacteria growth. The cultures started in a 1.9 ml culture of TSB with 100 microliters of the selected pathogen. The cultures were then incubated with shaking at the desired temperature for growth.

On Day 4, the water agar plates were UV treated for 120 seconds. Here the soft agar was cooled so that the pathogens were not killed by the high temperature, but cooling stopped before the media solidified. For every 100 ml of soft agar, 100 ml of pathogen was added and gently mixed to avoid air bubbles. Ten ml of the pathogen was added onto the water agar plates that were UV treated. Once the soft agar solidified, the plates were wrapped with Parafilm and incubated at the required temperature for pathogen growth.

On Day 5, the data was collected to measure the zones of inhibition.

The results of in vitro inhibition assays were summarized in Table 5, which shows that 4 *Paenibacillus* strains show a broad inhibitory activity against the ESKAPE pathogens. In particular, MS2379 showed inhibitory activity against the two gram-positive bacteria (*E. faecium* and *S. aureus*). MS1479 and MS2820 show strong effects against a broad range of pathogens, with MS1479 against *E. faecium*, *S. aureus*, *E. cloacae*, *P. aeruginosa*, and *A. baumannii*, and MS 2820 against *K. pneumoniae*, *S. aureus*, *E. cloacae*, *P. aeruginosa*, and *A. baumannii* (Table 6).

TABLE 6

Results of in vitro inhibition against ESKAPE pathogens
ESKAPE Pathogen (Zone of Inhibition in cm)

| STRAINS | *Enterococcus faecium* ATCC 70021 | *Enterobacter cloacae* ATCC BAA-1143 Strain 55M | *Staphylococcus aureus* | *Pseudomonas aeruginosa* ATCC 27853 | *Acinetobacter baumannii* 3806 Walter Reed | *Klebsiella pneumoniae* 3363 Walter Reed |
|---|---|---|---|---|---|---|
| MS1479 | 0.1 | 0.2 | 0.9 | 0.1 | 0.4 | none |
| MS2379 | 0.3 | none | 1 | none | none | none |
| MS2414 | none | none | 0.6 | 0.1 | 0.3 | none |
| MS2820 | none | 0.5 | 0.7 | 0.2 | 0.4 | 0.3 |
| MS2337 | 0.3 | none | none | none | 0.2 | none |
| MS2341 | none | none | 0.5 | none | none | none |
| MS2697 | none | none | none | none | none | none |

Example 3 Analysis of the Produced Fusaricidin A

Extraction

Fermentation whole broth (each ~10-11 mL) was centrifuged at room temperature for 120 minutes at 3000 rpm. Supernatant was decanted, transferred to a separatory flask, and extracted with n-BuOH (2×7.5 mL) to yield crude n-BuOH extracts. For MeOH extraction, cell pellets were soaked in MeOH (2×10 mL), sonicated for 30 minutes, kept at room temperature for 12 hours, and then centrifuged at room temperature for 30 minutes at 3000 rpm. The clear supernatant was decanted, and MeOH was evaporated to yield crude extracts.

Sample Preparation for LC-MS Experiments 1-2 mg extracts were dissolved in 1-2 mL of HPLC grade MeOH, and filtered using 40 μm filters. Then 1 μL of analyte (concentration at 1 mg/mL) was injected into LC-QTOF-MS to obtain chromatograms. 1 mg fusaricidin A was dissolved in HPLC grade MeOH to prepare 1 mg/mL stock concentration, and then serial dilutions were made at 100, 10, 1, 0.1, 0.01 μg/mL. 1 μL of the analyte was injected into LC-QTOF-MS to obtain chromatograms. The detailed parameters for the LC-QTOF-MS analysis were listed in Table 7.

TABLE 7

UHPLC-QToF-MS Method:

UHPLC

| | |
|---|---|
| UHPLC | Agilent HPLC 1290 Series (Agilent Technologies, Palo Alto, CA, USA) |
| Column | Agilent Poroshell 120 EC-C18 2.7 μm, 2.1 × 150 mm |
| Mobile Phase | Water (A) + Acetonitrile (B), both containing 0.1% Formic acid (Gradient) |
| Flow Rate | 0.23 mL/min |
| Run time | 25 min |
| Injection Volume | 1 μL |

QToF-MS

| | |
|---|---|
| MS | Agilent QToF-MS 6530 series (Agilent Technologies, Palo Alto, CA, USA) |
| Ionization mode | ESI+ |
| Gas temperature | 325° C. |
| Gas Flow | 10 L/min |
| Nebulizer | 30 psig |
| Capillary voltage | 3.5 kV |
| Fragmentor | 125 V |
| Mass Range (m/z) | 100-1500 |

Each whole broth cultural sample was centrifuged to separate the supernatant from the cell pellets. The supernatant was extracted with n-butanol, and the cell pellets were extracted with methanol, producing n-butanol and methanol extracts respectively. The organic solvent extracts were analyzed by LC-MS for production of fusaricidins. Fusaricidin A was used as the baseline to generate a quantification curve based on the concentrations against the peak areas from positive ESIMS extracted ion chromatograms. The contents of fusaricidin A in these samples are summarized in Table 8-10. *Bacillus amyloliquefaciens* (Strain MS0633) was compared with *Paenibacillus* strains (MS2379, MS2414 and MS2820) in different media. As shown in Table 8, MS0633 produced negligible amounts of fusaricidin A in all media.

TABLE 8

Comparison of fusaricidin A productivities by *B. amyloliquefaciens* (Strain MS0633) and *Paenibacillus* spp. (MS2379, MS2414 and MS2820) in various media - SF070816.

| Strain | Medium | Total Fusaricidins A (mg/L) |
|---|---|---|
| MS0633 | GB6-M3 | <0.01 |
| | GB6-M10 | <0.01 |
| | GB6-M11 | <0.01 |
| MS2379 | GB6-M3 | 117.9 |
| | GB6-M10 | 192.8 |
| | GB6-M11 | 36.2 |

TABLE 8-continued

Comparison of fusaricidin A productivities by *B. amyloliquefaciens* (Strain MS0633) and *Paenibacillus* spp. (MS2379, MS2414 and MS2820) in various media - SF070816.

| Strain | Medium | Total Fusaricidins A (mg/L) |
|---|---|---|
| MS2414 | GB6-M3 | 234.6 |
| | GB6-M10 | 252.2 |
| | GB6-M11 | 292.9 |
| MS2820 | GB6-M3 | 118.9 |
| | GB6-M10 | 231.6 |
| | GB6-M11 | 17.6 |

The fusaricidin A concentrations in GB6-M10 medium using various yeast extracts are shown in Table 9. Without being bound by a theory, the yeast extracts in the culture media may affect the fusaricidin production.

TABLE 9

Effect of yeast extract on fusaricidin A production

| Strain | Yeast Extract in GB6-M10 Medium | Note | Total Fusaricidin A (mg/L) |
|---|---|---|---|
| MS2379 | Sigma 09182 | WB | 73.3 |
| | Sensient-Amberex 1003AG | WB | 80.7 |
| | Sensient-Amberex 695 | WB | 62.9 |
| | Lallemand-FNI100 | WB | 41.0 |
| | Biospringer - Springaline BA11/0-MG | WB | 104.4 |
| MS2414 | Sigma 09182 | WB | 70.4 |
| | Sensient-Amberex 1003AG | WB | 84.3 |
| | Sensient-Amberex 695 | WB | 79.1 |
| | Lallemand-FNI100 | WB | 78.8 |
| | Biospringer - Springaline BA11/0-MG | WB | 129.3 |
| MS2820 | Sigma 09182 | WB | 45.6 |
| | Sensient-Amberex 1003AG | WB | 40.3 |
| | Sensient-Amberex 695 | WB | 52.6 |
| | Lallemand-FNI100 | WB | 74.0 |
| | Biospringer - Springaline BA11/0-MG | WB | 84.0 |

Figure 3A:
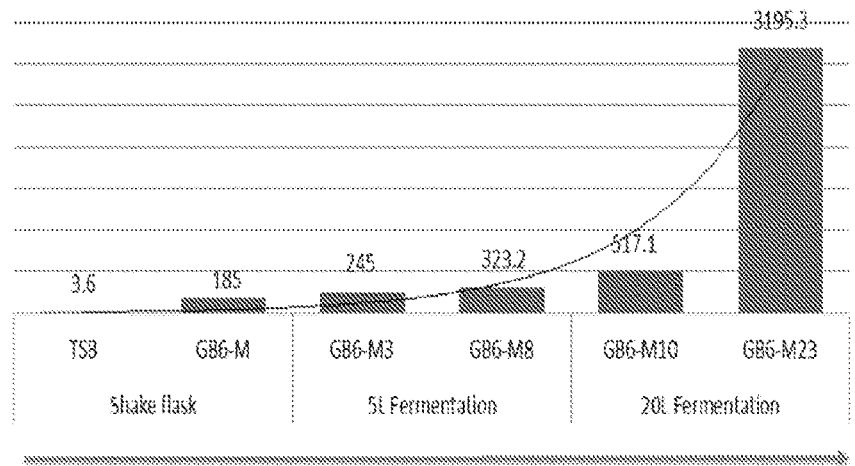
FIG. 3A shows the levels (mg/l) of fusaricidin A in different culture media and fermentation processes. TSB medium is a common lab medium used for screening isolates. GB6-M, GB6-M3, GB6-M8, and GB6-M10 are modified GB6-M media. GB6-M23 is 3× concentrated modified GB6-M10 using newly selected yeast extract.

The contents of fusaricidin A in the fermentation whole broth from 20 L fermentation are summarized in Table 10. The MeOH extracts of harvest WB of MS2414 in GB6-M23 medium and MS2379 in 3XGB6-M10 medium produced the highest content of fusaricidin A with production rates of 3195.26 mg/L and 419.70 mg/L, respectively. The effects of fermentation medium and process on the production of fusaricidin A are also shown in FIG. 3A.

TABLE 10

Fusaricidin A Productivity of Paenibacillus Strains in Various Media in 20L Fermentation

| Batch# | Strain | Medium | Fermentation Time (hour) | Total Fusaricidin A (mg/L) |
| --- | --- | --- | --- | --- |
| FER031516-Harvest | MS2379 | GB6-M8 | 72 | 358.3 |
| | MS2414 | GB6-M8 | 72 | 323.3 |
| FER032216-Harvest | MS2379 | GB6-M8 | 91 | 89.0 |
| | MS2414 | GB6-M8 | 91 | 233.3 |
| FER032916-Harvest | MS2379 | GB6-M8 | 78 | 44.1 |
| | MS2414 | GB6-M8 | 78 | 404.7 |
| FER041916-Harvest | MS2820 | GB6-M8 | 99 | 253.7 |
| | MS2414 | GB6-M8 | 72 | 226.3 |
| FER050316-Harvest | MS2379 | GB6-M10 | 76 | 609.8 |
| | MS2414 | GB6-M10 | 76 | 517.1 |
| FER051716-Harvest | MS2820 | GB6-M10 | 76 | 835.2 |
| | MS2414 | GB6-M10 | 76 | 334.2 |
| FER060716-Harvest | MS2379 | GB6-M10 | 76 | 297.5 |
| | MS2414 | GB6-M10 | 76 | 263.5 |
| FER061416-Harvest | MS2379 | GB6-M10 | 72 | 205.7 |
| | MS2414 | GB6-M10 | 72 | 45.8 |
| FER062916 | MS2379 | GB6-M10 | 24 | 32.8 |
| | MS2379 | GB6-M10 | 57 | 347.8 |
| | MS2414 | GB6-M10 | 24 | 32.3 |
| | MS2414 | GB6-M10 | 57 | 221.9 |
| FER072616 | MS2379 | 3x GB6-M10 | 96 | 419.7 |
| | MS2414 | 3x GB6-M10 | 96 | 369.2 |
| FER083016 | MS2379 | GB6-M20 | 96 | 292.6 |
| | MS2414 | GB6-M21 | 96 | 115.2 |
| FER100416 | MS2379 | GB6-M10 with AmberEx1003AG | 53 | <1 |
| | MS2414 | GB6-M10 with AmberEx1003AG | 53 | 75.3 |
| FER101816 | MS2379 | GB6-M22 | 24 | <1 |
| | | GB6-M22 | 48 | 23.7 |
| | | GB6-M22 | 78 | 113.7 |
| FER101816 | MS2414 | GB6-M23 | 24 | <1 |
| | | GB6-M23 | 48 | 49.4 |
| | | GB6-M23 | 78 | 3195.3 |

Figure 3B:
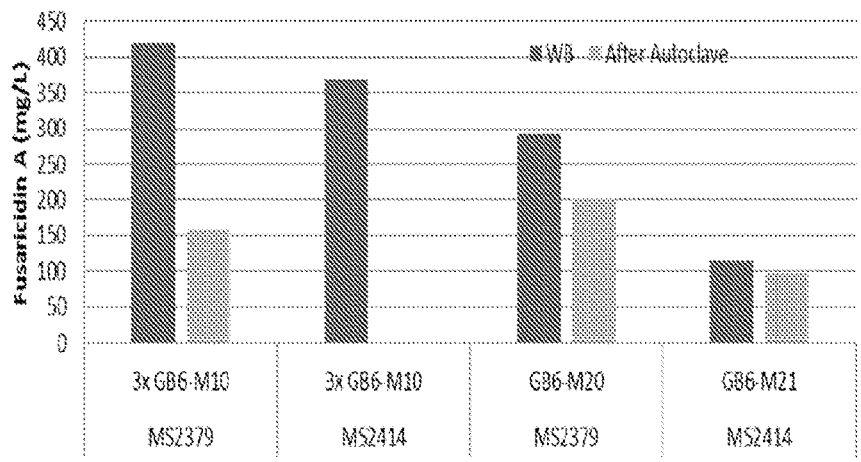
FIG. 3B shows the effect of autoclaving on the levels of fusaricidin A in whole broth ("WB"). The fermentation whole broth was autoclaved at 121.5° C. for 30 minutes, and fusaricidin contents were analyzed before and after autoclaving.

In order to test the heat stability of fusaricidins, the fermentation whole broth was autoclaved at 121.5° C. for 30 minutes. Fusaricidin contents were analyzed before and after autoclave. Without being bound by a theory, fusaricidin A is heat stable because significant amounts of fusaricidin A were detected after the harsh heat treatment in most cases (FIG. 3B).

The fermentation whole broth was concentrated by ultrafiltration using hollow fiber filter. The starting materials for concentration are fermentation whole broth of MS2379 and MS2414 in GB6-M10 medium (FER062916). After the WB was filtered through a PM-500 cartridge, the filtrate was further filtered using a PM-5 cartridge as shown in the Table 11:

TABLE 11

Parameters of cartridges

| WB/Retentate/Filtrate | Molecular Weight Range (Dalton) | Cells, enzymes or metabolites | Volume (mL) |
| --- | --- | --- | --- |
| Whole broth | | | 2000 |
| PM-500 Retentate | >500,000 | Cells, particles | 500 |
| PM-500 Permeate | <500,000 | Enzymes, metabolites | 1500 |
| PM-5 Retentate | 5,000-500,000 | Enzymes | 300 |
| PM-5 Permeate | <5,000 | Metabolites | 1200 |

PM-500 Cartridge: 500,000 cut-off
PM-5 Cartridge: 5,000 cut-off

Figure 4:
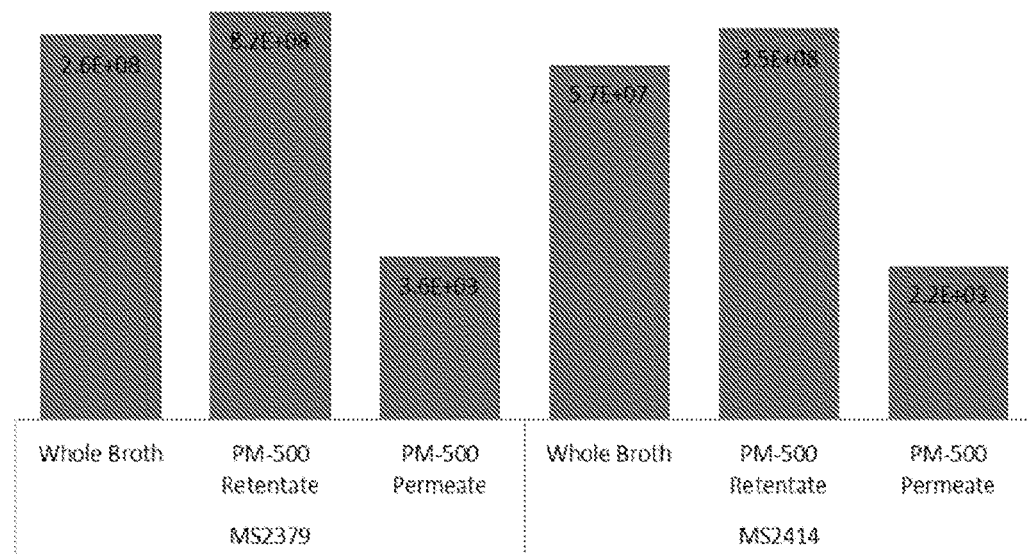
FIG. 4 shows the amounts of cells after ultrafiltration (CFU/ml) using PM-500 Cartridge (Molecular weight cut-off: 500 kDa) and PM-5 Cartridge (Molecular weight cut-off: 5 kDa). For MS2379, the amounts were 2.6 E+08 CFU/ml in whole broth, 8.2 E+08 CFU/ml in PM-500 retenate, and 3.6 E+03 CFU/ml PM-500 permeate. For MS2414, the amounts were 5.7 E+07 CFU/ml in whole broth, 3.5 E+08 CFU/ml in PM-500 retenate, and 2.2 E+03 CFU/ml PM-500 permeate.
Figure 5:
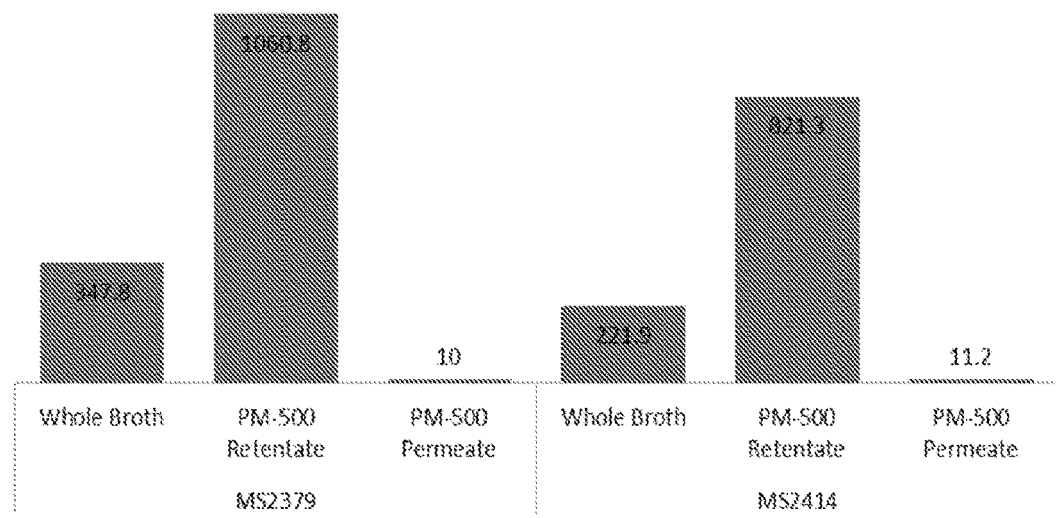
FIG. 5 shows the concentrations of fusaricidin A after ultrafiltration (mg/L) using PM-500 Cartridge (Molecular weight cut-off: 500 kDa) and PM-5 Cartridge (Molecular weight cut-off: 5 kDa). For MS2379, the concentrations of fusaricidin A were 347.8 mg/L in whole broth, 1060.8 mg/L in PM-500 retenate, and 10 mg/L PM-500 permeate. For MS2414, the concentrations of fusaricidin A were 221.9 mg/L in whole broth, 821.3 mg/L in PM-500 retenate, and 11.2 mg/L PM-500 permeate.

Cells and fusaricidins were both highly concentrated in PM-500 retentate along with the cell (FIGS. 4 and 5).

Example 4 Antimicrobial Activities of MS2414

Because of the strong antimicrobial activities shown by some fractions of microbial strain MS2414 (FIG. 6), the fractions of MS2414 extract were further fractioned to identify particular classes of compounds that contribute to the pathogen inhibition.

As shown in FIG. 6, organic extracts of microbial strain MS2414 in different fermentation media and column fractions from the extract of MS2414 in BS3-M2 demonstrated anti-microbial activities against several human fungal and bacterial pathogens, including *Candida albicans*, *Candida glabrata*, *Candida krusei*, *Aspergillus fumigatus*, *Cryptococcus neoformans*, *Staphylococcus aureus*, MRSA, *Escherichia coli*, *Pseudomonas aeruginosa*, and *Mycobacterium intracellulare*. Particularly, column fractions 131-135 and 136-152 of MS2414 extracts and n-BuOH and MeOH extracts of MS2414 showed antifungal activities that are comparable to commercial antifungal agents, e.g., Amphotericin B. Notably, the column fractions demonstrated more potent antifungal effects against *C. neoformans* than Amphotericin B. The methods to isolate and fraction the organic extracts are appreciated by one of ordinary skill in the art.

The potent activities against the fungal pathogen *C. neoformans* and the gram-positive bacteria *S. aureus*, MRSA, and *M. intracellulare* were also shown in the crude extracts (FIG. 7). Two column fractions (79H and 79I) exhibited remarkable activities against *C. neoformans* with IC50 values less than 0.06 μg/mL when compared to the antifungal drug amphotericin B with an IC50 of 0.15 μg/mL.

LC-MS analysis indicated that both 79H and 79I column fractions contain fusaricidin A as a predominant constituent (FIGS. 8A and 8B). Fusaricidin A accounts for approximate 57% and 31% of the respective fractions. Considering that cryptococcosis infection caused by *C. neoformans* is one of the most prevalent opportunistic invasive mycoses, affecting a large number of immunocompromised patients (e.g., AIDS patients), this disclosure may identify a new lead class of compounds that are effective in vivo for drug development. Moreover, the LC-MS analysis also shows that the column fractions (79H and 79I) also contain compounds other than fusaricidin A. Those compounds may also be related to the potent antifungal activities of the MS2414 column fractions, and may constitute a new group of antifungal agents. Therefore, the metabolites of this microbial strain and related strains have potential values not only for protecting agricultural crops, but also for pharmaceutical development.

Figure 9:
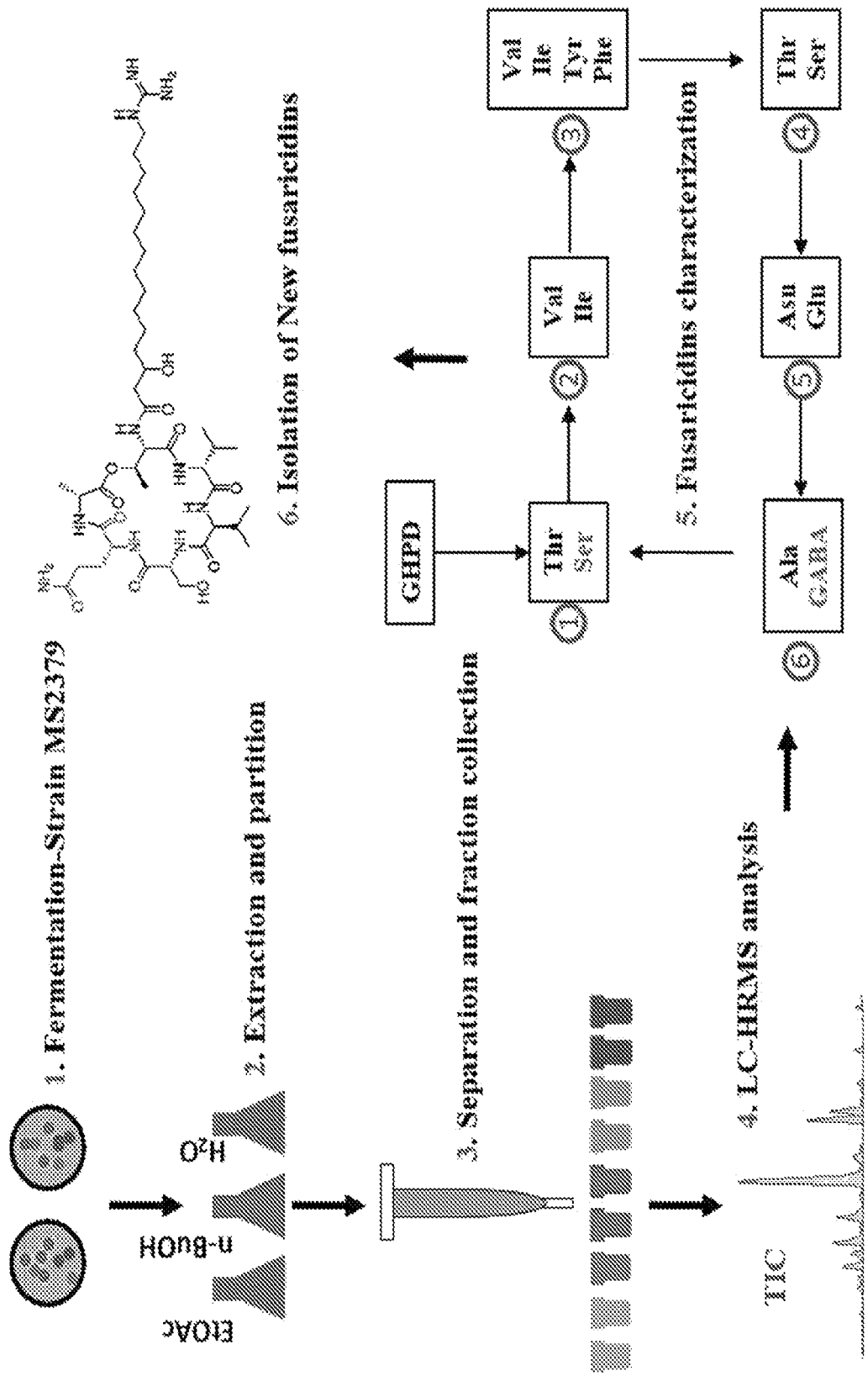
FIG. 9 shows a workflow for the identification of antifungal fusaricidins from *Paenibacillus* sp. MS2379.
Figure 10A:
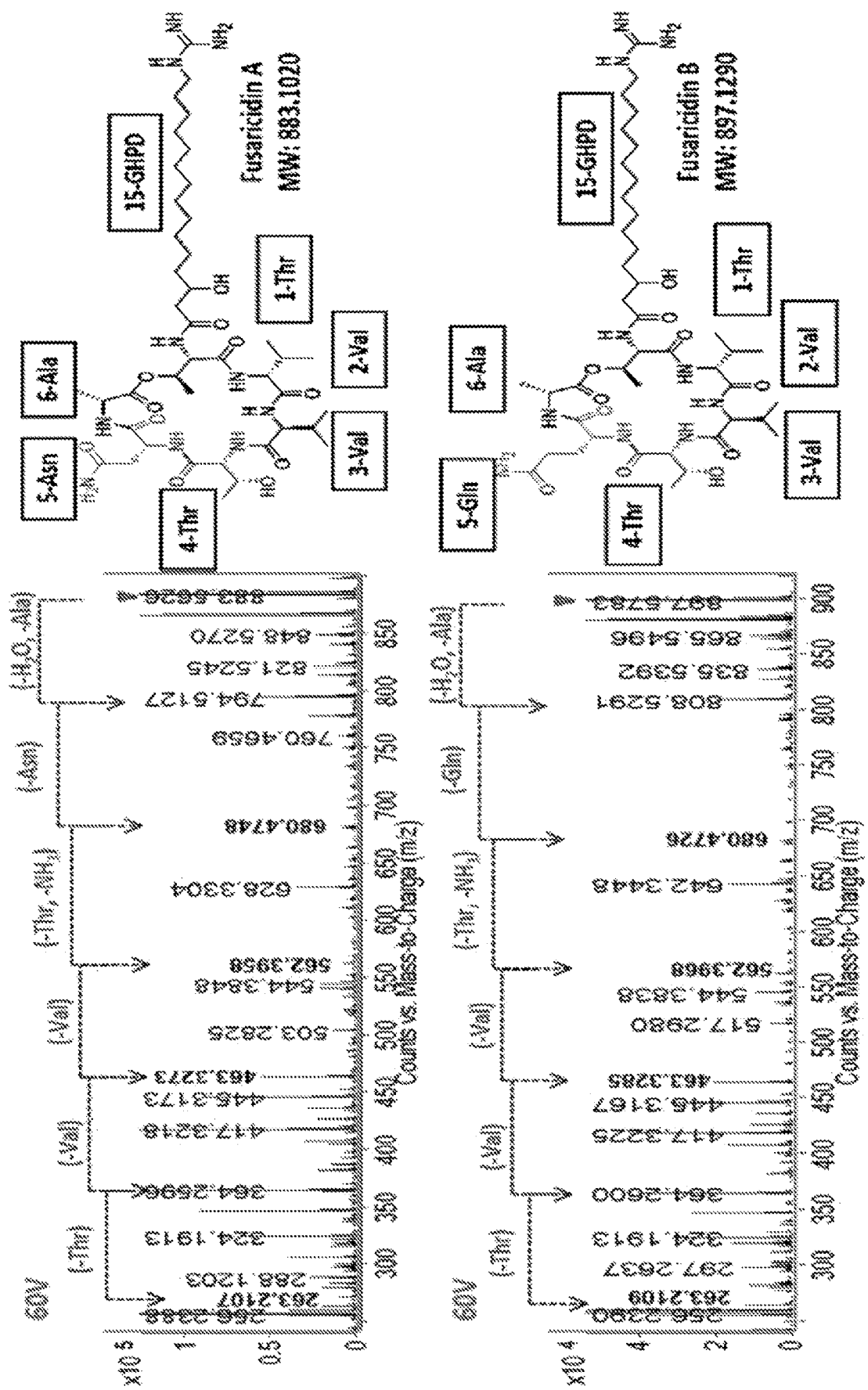
FIG. 10 shows the fragmentation patterns for cyclic fusaricidins A and B (FIG. 10A) and open-chain fusaricidins A and B (FIG. 10B).
Figure 10B:
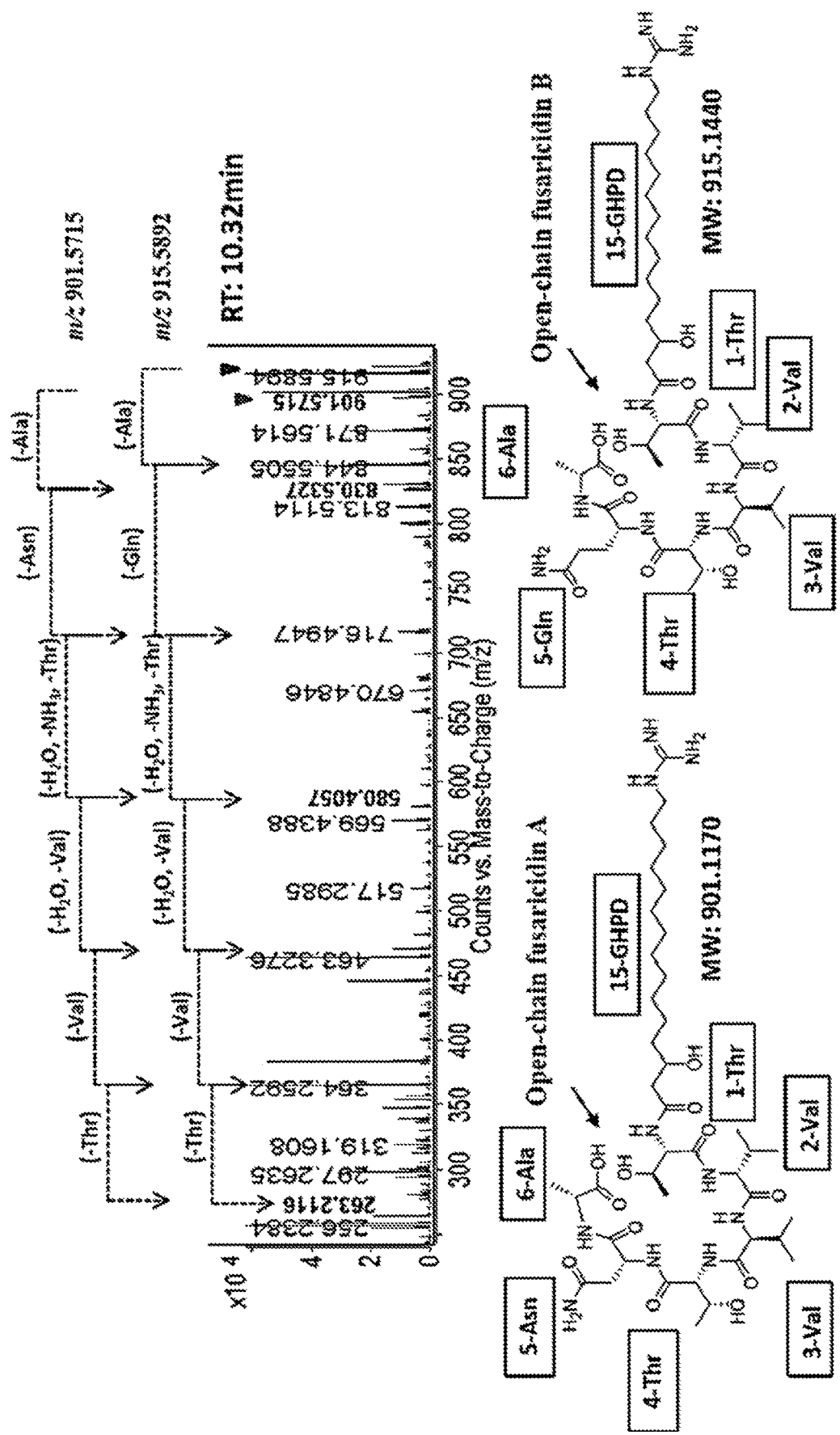

Example 5 Identification of Active Ingredients from the Bacterial Fermentation Broth Given the strong antimicrobial activity, the column fractions from the *Paenibacillus* strain fermentation broth were further isolated with UHPLC-HRESIMS and NMR techniques to identify active ingredients against microbes. An exemplary process of isolation is shown in FIG. 9, in which the n-butanol extract prepared from the fermentation broth of MS2379 was fractioned into column fractions (CFs) by reversed-phase Cis silica gel chromatography. The minor fusaricidins were enriched in these CFs, making it possible to be detected by UHPLC-HRESIMS. Prior to the UHPLC-HRESIMS analysis, the QTOF-MS collision energy was optimized as 60V that produced most fragmentation information for the reference compounds fusaricidins A and B. Open-chain fusaricidins A and B were also analyzed using the same conditions as the cyclic fusaricidins A and B (FIG. 10). The fragmentation patterns of the four compounds are the basis for the analysis of other fusaricidins. Generally, sequential elimination of amino acid residues starting from alanine (position 6) is observed for cyclic fusaricidins, which is accompanied by the elimination of $H_2O$ and $NH_3$ from the fatty acid side chain. For the open-chain fusaricidins, elimination of an additional $H_2O$ is the most characteristic feature during the fragmentation process.

Figure 11A:
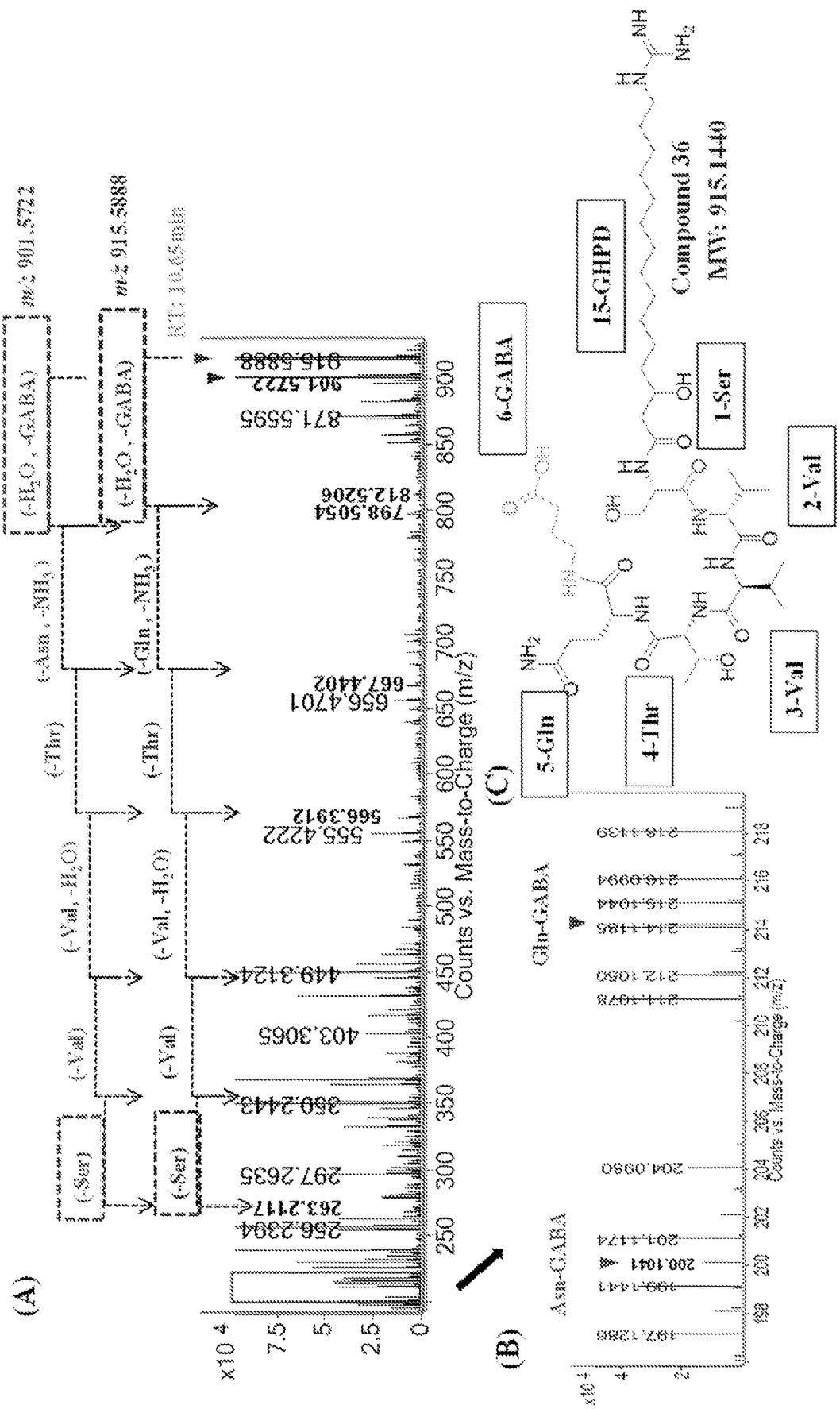
FIG. 11A shows the $MS^2$ spectra of fusaricidins 34 and 36 with Ser at position-1 and GABA at position-6.
Figure 11B:
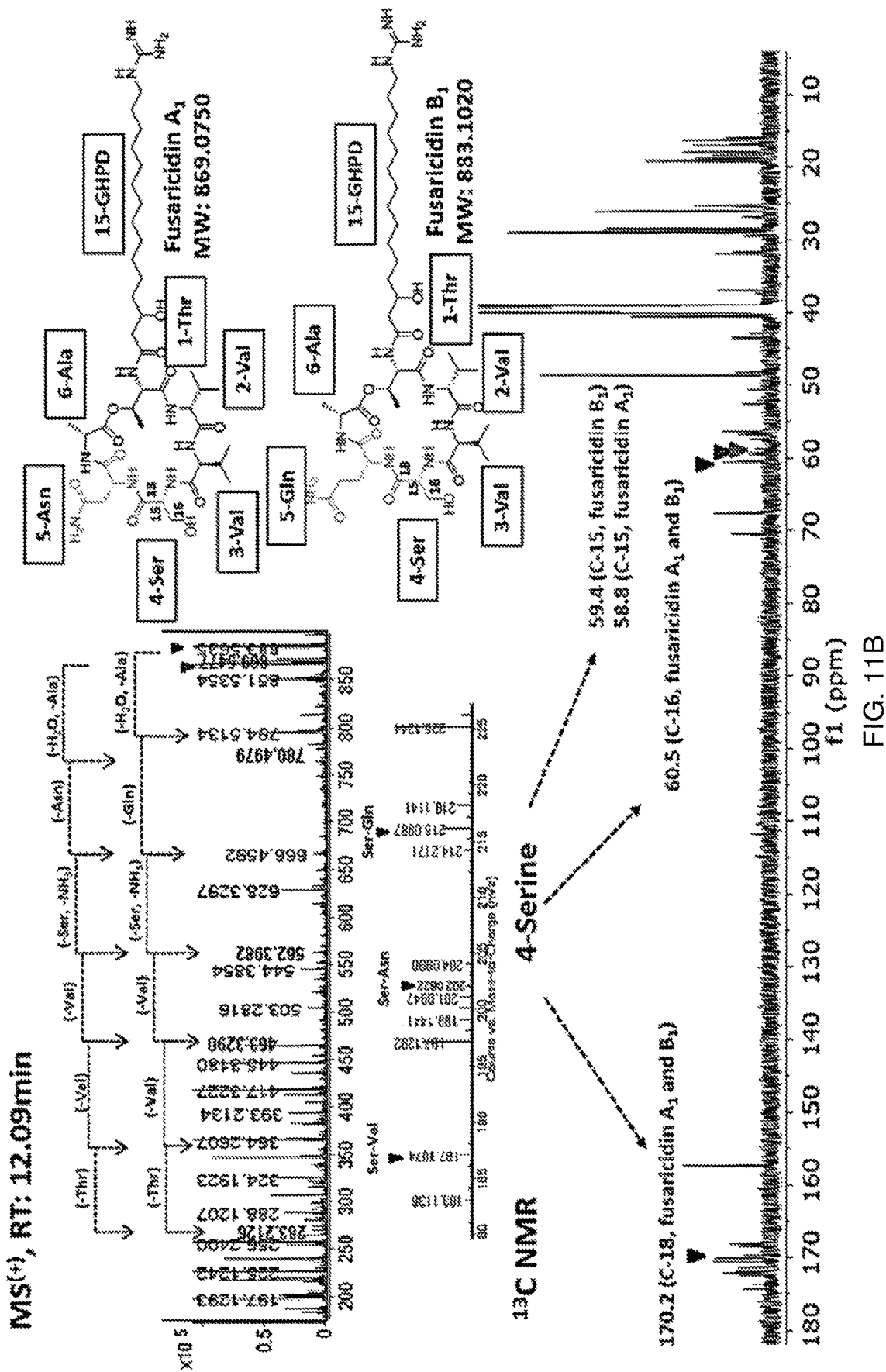
FIG. 11B shows $MS^2$ and 13C NMR spectra of fusaricidins $A_1$ and $B_1$ (FIG. 11B).

As a result, a total of 54 fusaricidins were identified, with fusaricidins A and B being the major compounds accounting for 27% and 26%, respectively, of the total fusaricidins (Table 1). In addition, 27 new fusaricidins (each with a content ≤2.5% of the total fusaricidins) were characterized through careful analysis of the HRESIMS fragmentation patterns. The structural characterization of the new fusaricidins by HRESIMS was validated by follow-up isolation and NMR spectroscopic analysis of representative compounds. For example, compounds 32 and 34 with amino acids of serine (position 1) and GABA (position 6) is illustrated in FIG. 11A. In addition, new compounds—fusaricidins $A_1$ and $B_1$—have also been isolated with their structures confirmed by 2D NMR.

Example 6 Anti-Microbial Activities of Fusaricidins

The antimicrobial activities of identified fusaricidins were in an in vitro study against several clinically relevant microbes. As shown in Tables 12-14, fusaricidins A, B, A1 and B1 demonstrates strong inhibitions against various clinical relevant bacteria (e.g., *S. aureus, E. faecium, E. coli* and *P. aeruginosa*), fungi (e.g., *C. neoformans, C. albicans,* and *A. fumigatus*), and parasites (e.g., *L. donovani* and *T. brucei*). For the in-vitro assays against bacteria, fusaricidins were tested against methicillin-resistant *Staphylococcus aureus*, vancomycin-resistant *Enterococcus faecium, Escherichia coli*, and *Pseudomonas aeruginosa* using four antibacterial drugs methicillin, vancomycin, cefotaxime, and meropenem as controls. It appears that fusaricidins A and B showed a strong activity against the gram-positive bacteria MRSA, and VRE with fusaricidin A is more potent than fusaricidins B, $A_1$, and $B_1$ (Table 12). Fusaricidins were also tested against fungal pathogens *Cryptococcus neoformans, Candida albicans*, and *Aspergillus fumigatus* and compared with two antifungal drugs, fluconazole and amphotericin B (Table 13). Moreover, the anti-parasitic activity was also tested against *L. donovani* and *T. brucei* (Table 14).

TABLE 12

In-vitro anti-fungal activities of fusaricidins A, A1, B, and B1[a]

| | $IC_{50}$[b] ($MIC$[c]), µg/mL | | |
| --- | --- | --- | --- |
| Compound | *C. neoformans* | *C. albicans* | *A. fumigatus* |
| Fusaricidin A (RRR-8-32Q) | 1.2/2.5 | 3.5/5.0 | 18.5/>20 |
| Fusaricidin A (SQ-1-43 A) | 0.5/1.3 | 5.1/10.0 | >20/>20 |
| Fusaricidin B (SQ-1-43B) | 1.1/2.5 | 9.1/10.0 | >20/>20 |
| Fusaricidin $A_1/B_1$ (SQ-1-43B)[d] | 16.0/>20 | >20>20 | >20>20 |
| Fluconazol (positive control) | 2.5/6.3 | 1.0/1.6 | >100/>100 |
| Amphotericin B (positive control) | 0.3/0.4 | 0.4/0.8 | 2.4/3.1 |

[a]The highest test concentrations for fusaricidins A and B, fluconazole, and amphotericin B are 20, 100, and 100 µg/mL, respectively.
[b]50% growth inhibitory concentration.
[c]Minimum inhibitory concentration (the lowest concentration that allows no detectable growth).
[d]A mixture of A1 and B1 in a ration of 1:3.

TABLE 13

In-vitro anti-bacterial activities of fusaricidins A, A1, B, and B1[a]

| | $IC_{50}$[b] ($MIC$[c]), µg/mL | | | |
| --- | --- | --- | --- | --- |
| Compound | MRSA[d] | VRE[e] | *E. coli*[f] | *P. aeruginosa*[g] |
| Fusaricidin A (RRR-8-32Q) | 2.1/2.5 | 3.7/5.0 | >20/>20 | >20/>20 |
| Fusaricidin A (SQ-1-43 A) | 2.3/2.5 | 3.6/5.0 | >20/>20 | >20/>20 |
| Fusaricidin B (SQ-1-43B) | 4.2/5.0 | 8.7/20.0 | >20/>20 | >20/>20 |
| Fusaricidin $A_1/B_1$ (SQ-1-43B)[h] | >20/>20 | >20/>20 | >20/>20 | >20/>20 |
| Methicillin (positive control) | 12.1/50.0 | >100/>100 | >100/>100 | 76.0/>100 |
| Vancomycin (positive control) | 1.3/1.6 | >100/>100 | 62.3/>100 | >100/>100 |
| Cefotaxime (positive control) | 15.6/25.0 | >100/>100 | >100/>100 | 5.3/25.0 |
| Meropenem (positive control) | 5.7/12.5 | >100/>100 | 5.4/12.5 | 5.9/25.0 |

[a]The highest test concentrations for fusaricidins A and B and the four positive controls are 20 and 100 µg/mL, respectively.
[b]50% growth inhibitory concentration.
[c]Minimum inhibitory concentration (the lowest concentration that allows no detectable growth).
[d]Methicillin-resistant *Staphylococcus aureus* ATCC 1708.
[e]Vancomycin-resistant *Enterococcus faecium* ATCC 700221.
[f]*Escherichia coli* ATCC 2452.
[g]*Pseudomonas aeruginosa* ATCC 2108.
[h]A mixture of $A_1$ and $B_1$ in a ratio of 1:3.

TABLE 14

In-vitro antiparasitic activities of fusaricidins A[a]

| Compound | $IC_{50}^{b}/IC_{90}^{c}$, μg/mL | | | | |
|---|---|---|---|---|---|
| | L. donovani Promastigote | L. donovani Amastigote | L. donovani Amastigote/THP | T. brucei | THP-1 |
| Fusaricidin A | 3.1/6.7 | >10 />10 | 2.7/8.8 | 0.11/0.13 | >10/>10 |
| Amphotericin B | 0.3/0.4 | 0.9/1.1 | 0.2/0.2 | nt[d] | >2/>2 |
| α-Difluoromethylornithine | nt[d] | nt[d] | nt[d] | 5.7/6.6 | nt[d] |

[a]The highest test concentrations for fusaricidin A, amphotericin B, and α-difluoromethylornithine (DFMO) are 10, 2 and 20 μg/mL, respectively.
[b]50% inhibitory concentration.
[c]90% inhibitory concentration.
[d]Not tested.

EQUIVALENTS

It should be understood that although the present disclosure has been specifically disclosed by certain embodiments and optional features, modification, improvement, and variation of the disclosures embodied disclosed herein may be resorted to by those skilled in the art, and that such modifications, improvements, and variations are considered to be within the scope of this disclosure. The materials, methods, and examples provided here are representative of certain embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

Throughout this disclosure, various publications, patents, and published patent specifications are referenced by an identifying citation. All publications, patent applications, patents, and other references mentioned herein are expressly incorporated by reference in their entirety, to the same extent as if each were incorporated by reference individually. In case of conflict, the present specification, including definitions, will control.

Other embodiments are set forth in the following claims.

What is claimed is:

1. A method of treating a pathogen in a human, comprising administering to the human a composition comprising an effective amount of a cyclic fusaricidin compound and an open-chain fusaricidin compound, wherein the cyclic fusaricidin compound has a mass range (m/z) value of less than 880.0 or wherein the cyclic fusaricidin compound has Formula I:

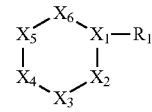

wherein $X_1$ is Ser, $X_2$ is Val or Ile, $X_3$ is selected from the group consisting of Ile, Tyr, Val, and Phe, $X_4$ is Thr or Ser, $X_5$ is Asn or Gln, $X_6$ is Ala,
wherein $R_1$ is a 15-guanidino-3-hydroxypentadecanoyl (GHPD) side chain or 17-guanidino-3-(R)-hydroxyheptadecanoyl (GHHD) side chain, and
wherein the open-chain fusaricidin compound has Formula II:

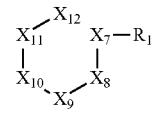

wherein $X_7$ is Thr or Ser; $X_8$ is Val or Ile; $X_9$ is selected from the group consisting of Val, Ile, Tyr, and Phe; $X_{10}$ is Thr or Ser; $X_{11}$ is Asn or Gln; $X_{12}$ is selected from the group consisting of Ala, GABA, and Gly;
wherein $R_1$ is a GHPD side chain,
and wherein the pathogen is (i) a bacterium selected from a Gram-positive bacterium, E. coli, and P. aeruginosa, (ii) a fungus, or (iii) a parasite selected from L. donovani and T brucei.

2. The method of claim 1, wherein the composition is obtained from a whole culture broth comprising one or more bacteria, from a whole broth sterile filtrate from the one or more bacteria, or from a cell pellet of the one or more bacteria.

3. The method of claim 1, wherein $X_1$ is Ser; $X_2$ is Val; $X_3$ is Ile, Tyr, Val, or Phe; $X_4$ is Thr or Ser; $X_5$ is Asn; wherein $R_1$ is a GHPD side chain for the cyclic fusaricidin.

4. The method of claim 1, wherein the cyclic fusaricidin comprises one or both of fusaricidin $A_1$ and fusaricidin $B_1$.

5. The method of claim 1, wherein $X_1$ is Ser; $X_2$ is Val; $X_3$ is Ile, Tyr, or Phe; $X_4$ is Thr or Ser; $X_5$ is Gln; wherein $R_1$ is a GHPD side chain for the cyclic fusaricidin.

6. The method of claim 1, wherein $X_1$ is Ser; $X_2$ is Val; $X_3$ is Ile, Tyr, Val, or Phe; $X_4$ is Thr or Ser; $X_5$ is Gln; wherein $R_1$ is a GHPD side chain for the cyclic fusaricidin.

7. The method of claim 1, wherein the pathogen is selected from the group consisting of *C. neoformans, C. albicans, A. fumigatus, S. aureus, E. faecium, E. coli, P. aeruginosa, L. donovani*, and *T brucei*.

8. The method of claim 1, wherein the composition is obtained from MS2379 or MS2414.

9. A method of treating a pathogen in a human, comprising administering to the human an effective amount of *Paenibacillus* and/or *Bacillus* bacteria, the bacteria comprising one or more of MS1479 (ATCC Accession No. PTA-124701), MS2379 (ATCC Accession No. PTA-124703), MS2414 (ATCC Accession No. PTA-124704), MS2820 (ATCC Accession No. PTA-124710), MS0633 (ATCC Accession No. PTA-124700), MS2335 (ATCC Accession No. PTA-124702), MS2652 (ATCC Accession No. PTA-124705), MS2658 (ATCC Accession No. PTA-124706), MS2681 (ATCC Accession No. PTA-124707), MS2697 (ATCC Accession No. PTA-124708), and MS2712 (ATCC Accession No. PTA-124709), wherein the pathogen is (i) a bacterium selected from a Gram-positive bacterium, *E. coli*, and *P. aeruginosa*; (ii) a fungus; or (iii) a parasite selected from *L. donovani* and *T brucei*.

10. The method of claim 9, wherein the pathogen is selected from the group consisting of *C. neoformans, C. albicans, A. fumigatus, S. aureus, E. faecium, E. coli, P. aeruginosa, L. donovani*, and *T brucei*.

11. The method of claim 9, wherein the bacteria comprise MS2379 or MS2414.

\* \* \* \* \*